(12) United States Patent
Jokhadze et al.

(10) Patent No.: US 10,195,569 B2
(45) Date of Patent: *Feb. 5, 2019

(54) SPIN COLUMNS COMPRISING POLY(ACID) MEMBRANE SEPARATION MATRICES, AND METHODS OF MAKING AND USING THE SAME

(71) Applicant: Takara Bio USA, Inc., Mountain View, CA (US)

(72) Inventors: George G. Jokhadze, Mountain View, CA (US); Sayantan Mitra, Mountain View, CA (US)

(73) Assignee: TAKARA BIO USA, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/703,892

(22) Filed: Sep. 13, 2017

(65) Prior Publication Data

US 2018/0001266 A1 Jan. 4, 2018

Related U.S. Application Data

(63) Continuation of application No. 14/582,108, filed on Dec. 23, 2014, now Pat. No. 9,895,665.

(60) Provisional application No. 62/007,798, filed on Jun. 4, 2014, provisional application No. 61/943,174, filed on Feb. 21, 2014.

(51) Int. Cl.
*B01D 63/16* (2006.01)
*B01D 71/56* (2006.01)
*C07K 1/14* (2006.01)
*C07K 1/22* (2006.01)

(52) U.S. Cl.
CPC .............. *B01D 63/16* (2013.01); *B01D 71/56* (2013.01); *C07K 1/14* (2013.01); *B01D 2315/02* (2013.01); *B01D 2317/02* (2013.01); *C07K 1/22* (2013.01)

(58) Field of Classification Search
CPC .................................. B01D 71/56; C07K 1/14
USPC ............................................................ 422/72
See application file for complete search history.

(56) References Cited

U.S. PATENT DOCUMENTS

| 4,755,356 A | 7/1988 | Robbins et al. |
| 6,221,614 B1 | 4/2001 | Prusiner et al. |
| 6,402,918 B1 | 6/2002 | Schlenoff et al. |

(Continued)

FOREIGN PATENT DOCUMENTS

| CA | 2068220 A1 | 5/1991 |
| EP | 2376523 A1 | 10/2011 |

(Continued)

OTHER PUBLICATIONS

Bhattacharjee, S. et al. (2012). Formation of High-Capacity Protein-Adsorbing Membranes Through Simple Adsorption of Poly(Acrylic acid)-Containing Films at low pH. Langmuir 28(17):6885-6892. (Year: 2012).*

(Continued)

*Primary Examiner* — Jill A Warden
*Assistant Examiner* — Jacqueline Brazin
(74) *Attorney, Agent, or Firm* — Otto C. Guedelhoefer IV; Bret E. Field; Bozicevic, Field & Francis LLP

(57) ABSTRACT

Spin columns that include a poly(acid) membrane separation matrix are provided. Also provided are kits that include the subject devices, as well as methods of using the devices, e.g., in sample preparation (such as protein purification) protocols.

21 Claims, 9 Drawing Sheets

(56) References Cited

U.S. PATENT DOCUMENTS

| | | | |
|---|---|---|---|
| 6,620,629 | B1 | 9/2003 | Prusiner et al. |
| 6,703,498 | B2 | 3/2004 | Tchaga |
| 6,869,938 | B1 | 3/2005 | Schwartz et al. |
| 8,349,764 | B2 | 1/2013 | Burba, III |
| 8,377,394 | B2 | 2/2013 | Sakowski et al. |
| 2004/0063153 | A1 | 4/2004 | Jelinek et al. |
| 2004/0138414 | A1* | 7/2004 | Yue .................. C07K 14/47 530/350 |
| 2004/0180415 | A1 | 9/2004 | Tchaga et al. |
| 2007/0161785 | A1 | 7/2007 | Tchaga et al. |
| 2008/0300397 | A1 | 12/2008 | Kenrick et al. |
| 2009/0313813 | A1 | 12/2009 | Sato et al. |
| 2011/0124101 | A1 | 5/2011 | Urthaler et al. |
| 2011/0253616 | A1 | 10/2011 | Childs et al. |
| 2013/0244338 | A1* | 9/2013 | Bruening ................. G01N 1/34 436/177 |

FOREIGN PATENT DOCUMENTS

| | | |
|---|---|---|
| JP | 2002-539081 A | 11/2002 |
| JP | 2004-529314 A | 9/2004 |
| JP | 2011-502045 A | 1/2011 |
| WO | WO 00/55185 A1 | 9/2000 |
| WO | WO 2005/120700 A2 | 12/2005 |
| WO | WO 2007/140294 A2 | 12/2007 |
| WO | WO 2008/075194 A2 | 6/2008 |
| WO | WO 2010/082894 A1 | 7/2010 |
| WO | WO 2013/059526 A1 | 4/2013 |
| WO | WO 2013/180648 A1 | 12/2013 |

OTHER PUBLICATIONS

Dai, J. et al. (2006). High-Capacity Binding of Proteins by Poly(Acrylic Acid) Brushes and Their Derivatives. Langmuir. 22, 4274-4281. (Year: 2006).*

Ma, Z. et al. (2008). Electrospun regenerated cellulose nanofiber affinity membrane functionalized with protein A/G for IgG purification. J Membrane Sci. 319(1-2), 23-28. (Year: 2008).*

Anuraj et al. "An All Aqueous Route to Polymer Brush-Modified Membranes with Remarkable Permeabilities and Protein Capture Rates," J. Memb. Sci. (Feb. 1, 2012) 389: 117-125.

Bhattacharjee, S. "Formation of High-Capacity Protein-Adsorbing Membranes Through Simple Adsorption of Poly(acrylic acid)-Containing Films at low pH," Langmuir. 28(17):6885-6892 (May 1, 2012).

Dai et al. "High-Capacity Binding of Proteins by Poly(Acrylic Acid) Brushes and Their Derivatives," Langmuir, 2006, vol. 22, No. 9, pp. 4274-4281.

Gaberc-Porekar et al. "Perspectives of immobilized-metal affinity chromatography," Journal of Biomedical and Biophysical Methods, 2001, vol. 49, No. 1, pp. 335-360.

Jain et al. "Completely Aqueous Procedure for the Growth of Polymer Brushes on Polymeric Substrates," Langmuir (2007) 23:11360-11365.

Jain et al. "Protein Purification with Polymeric Affinity Membranes Containing Functionalized Poly(acid) Brushes," Biomacromolecules (Apr. 12, 2010), 11:1019-1026.

Ma et al. "Electrospun regenerated cellulose nanofiber affinity membrane functionalized with protein A/G for IgG purification", vol. 319, Issues 1-2, Jul. 1, 2008, pp. 23-28.

Pang et al. "Pepsin-Containing Membranes for Controlled Monoclonal Antibody Digestion Prior to Mass Spectrometry Analysis", Anal. Chem. Nov. 3, 2015; 87(21): 10942-10949.

Sartorius Stedim Biotech GMBH "Operating Instructions: Vivapure Ion Exchange Vivapure Mini & Maxi Spin Columns," Publication No. SLU6101-e11115, Nov. 2011, Goettingen, Germany, 10 pages.

Tan et al. "Limited Proteolysis via Millisecond Digestions in Protease-Modified Membranes," Anal. Chem. Oct. 2, 2012; 84(19): 8357-8363.

Xu et al. "Facile Trypsin Immobilization in Polymeric Membranes for Rapid, Efficient Protein Digestion," Anal. Chem. 2010, 82 (24), pp. 10045-10051.

Kökpinar et al. "Innovative modular membrane adsorber system for high-throughput downstream screening for protein purification," Biotechnology Progress, vol. 22, No. 4, Aug. 4, 2006, pp. 1215-1219.

Li Shuwei, ed."Further separation and purification of protein samples," Biochemistry, Beijing University of Post and Telecommunications Press, 1st Edition, Sep. 2012, pp. 355-357. (Partial translation only).

Ramakrishna et al. "Polymer Membranes in Biotechnology: Preparation, Functionalization and Application," © 2011 by Imperial College Press, pp. 201-206.

Xu, Dan: "Electrospun Affinity Membrane for Immunoglobin G Purification," Thesis submitted for the Degree of Master of Science Graduate Program in Bioengineering National University of Singapore, 2006, p. 72.

* cited by examiner 1. 1 mg/ml; 2. 0.8 mg/mL; 3. 0.6 mg/mL; 4. 0.4 mg/mL; 5. 0.2 mg/mL;
6. LBL flow through; 7. LBL elution; 8. brush flow through; 9. brush elution.

SPIN COLUMNS COMPRISING POLY(ACID) MEMBRANE SEPARATION MATRICES, AND METHODS OF MAKING AND USING THE SAME

CROSS REFERENCE To RELATED APPLICATIONS

This application is a continuation of U.S. patent application Ser. No. 14/582,108 filed Dec. 23, 2014, which application, pursuant to 35 U.S.C. § 119 (e), claims priority to the filing date of the U.S. Provisional Patent Application Ser. No. 61/943,174, filed Feb. 21, 2014 and U.S. Provisional Patent Application Ser. No. 62/007,798, filed Jun. 4, 2014; the disclosure of which applications are herein incorporated by reference.

INTRODUCTION

Purifying proteins from heterogeneous mixtures is often a multistep process using the physical, chemical, and electrical properties of the proteins to be purified. Important characteristics of a protein which are relevant for the purification are the solubility, the charge, the size, and the specific binding capacity of the protein. The isolation and cleanup of proteins is therefore a particular challenge, owing to the different chemical and physical properties of these biomolecules. Also, the materials from which the proteins are isolated and also the subsequent applications of the isolated proteins are diverse. It is therefore of interest to extend the already existing techniques for purifying and isolating proteins.

SUMMARY

Spin columns that include a poly(acid) membrane separation matrix are provided. Also provided are kits that include the subject devices, as well as methods of using the devices, e.g., in sample preparation (such as protein purification) protocols.

DEFINITIONS

Figure 1:
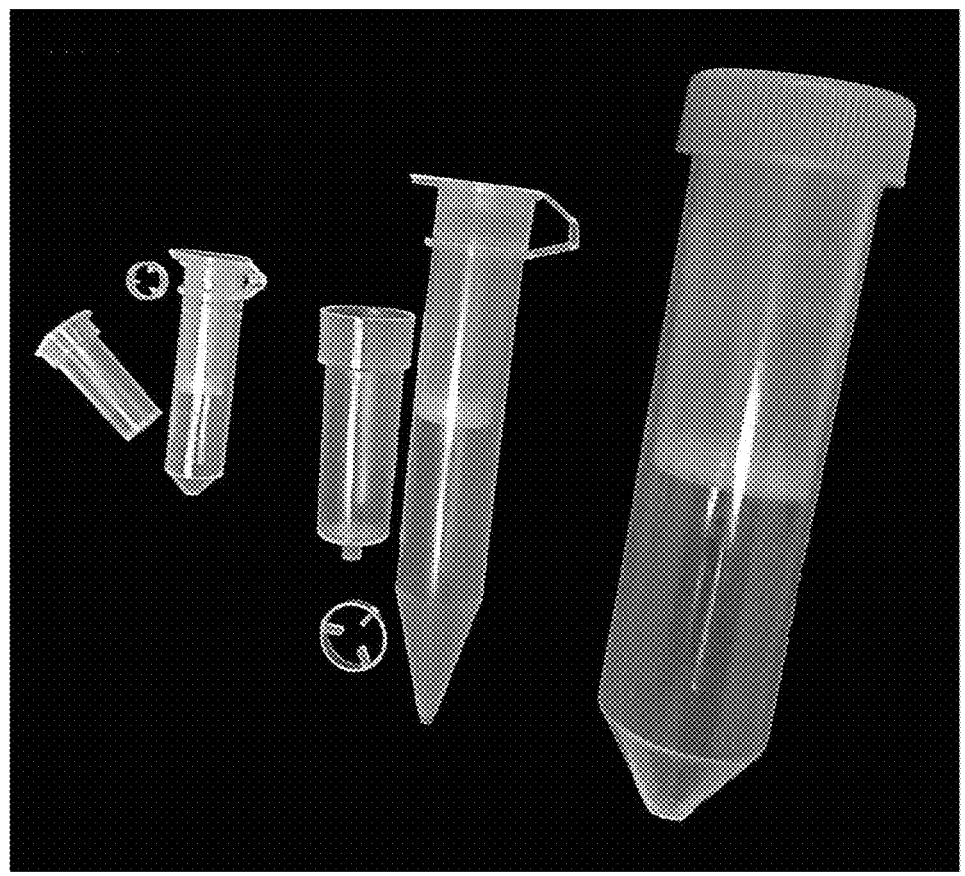
FIG. 1 provides views of various spin column configurations, including spin columns configured to fit into collection tubes.

Unless defined otherwise, all technical and scientific terms used herein have the same meaning as commonly understood by one of ordinary skill in the art to which this invention belongs. Still, certain elements are defined below for the sake of clarity and ease of reference.

The phrase "metal ion affinity composition" refers to a composition of matter having a polymeric matrix bonded to ligand/metal ion complexes. Metal ion affinity compositions of the present disclosure may vary and in some cases make use of a chelating agent, e.g., a ligand, that immobilizes a metal ion to from a ligand/metal ion complex. Chelating agents of the present disclosure may vary and include those agents capable of acting as multidentate ligands, e.g., polydentate chelating ligands, didentate chelating ligands, tridentate chelating ligands, tetradentate chelating ligands, pentadentate chelating ligands, hetaxdentate chelating ligands, etc.

The phrase "chelating ligand" is used herein interchangeably with the term "ligand". In some instances, the term ligand is used to refer to the individual interactions, i.e. individual bonds, between a multidentate ligand and the central atom to which it binds. For example, a tridentate chelating ligand may be referred to as having three ligands or forming a structure having three ligands with a central atom, e.g., a metal ion. Such ligand bonds are reversible and thus such ligand/central atom complexes may be associated and disassociated, e.g., by changing the environmental conditions within which the chelating ligand and the central atom are present. Central atoms of such complexes may be metal ions (described in greater detail below) and may thus form ligand/metal ion complexes. In certain instances, such ligand/metal ion complexes have affinity for particular proteins or particular protein motifs, e.g., a metal ion affinity peptide.

The compositions may be charged or uncharged. A composition is charged when the ligands thereof are complexed with metal ions. Conversely, a complex is uncharged when the ligands thereof are uncomplexed or free of metal ions, but may be complexed with metal ions.

The phrase "metal ion source" refers to a composition of matter, such as a fluid composition, that includes metal ions. As used herein, the term "metal ion" refers to any metal ion for which the affinity peptide has affinity and that can be used for purification or immobilization of a fusion protein. Such metal ions include, but are not limited to, $Ni^{2+}$, $Co^{2+}$, $Fe^{3+}$, $Al^{3+}$, $Zn^{2+}$ and $Cu^{2+}$. As used herein, the term "hard metal ion" refers to a metal ion that shows a binding preference for oxygen. Hard metal ions include $Fe^{3+}$, $Ca^{2+}$, and $Al^{3+}$. As used herein, the term "soft metal ion" refers to a metal ion that shows a binding preference of sulfur. Soft metal ions include $Cu^+$, $Hg^{2+}$, and $Ag^+$. As used herein, the term "intermediate metal ion" refers to a metal ion that coordinates nitrogen, oxygen, and sulfur. Intermediate metal ions include $Cu^{2+}$, $Ni^{2+}$, $Zn^{2+}$, and $Co^{2+}$.

As used herein, the term "contacting" means to bring or put together. As such, a first item is contacted with a second item when the two items are brought or put together, e.g., by touching them to each other.

The term "sample" as used herein refers to a fluid composition, where in certain embodiments the fluid composition is an aqueous composition. As used herein, a sample may be a research experiment sample, e.g., a sample generated in a research laboratory.

As used herein, the phrase "in the presence of" means that an event occurs when an item is present. For example, if two components are mixed in the presence of a third component, all three components are mixed together.

The phrase "oxidation state" is used in its conventional sense, see e.g., Pauling, General Chemistry (Dover Publications, NY.) (1988).

The terms "affinity peptide," "high affinity peptide," and "metal ion affinity peptide" are used interchangeably herein to refer to peptides that bind to a metal ion, such as a histidine-rich or HAT peptides. The term "affinity tagged polypeptide" refers to any polypeptide, including proteins, to which an affinity peptide is fused, e.g., for the purpose of purification or immobilization.

The terms "heteropolymer" and "copolymer" are used interchangeably herein to refer to those polymers derived from at least two species of constituent units, i.e. monomers, and may be defined as to how the different species of constituent units are arranged. For example, copolymers may be alternating copolymers wherein each unit of the copolymer alternates with one or more different units (e.g., -X-Y-(X-Y-)$_n$ . . . , -X-Y-Z-(X-Y-Z-)$_n$ . . . , etc.). Alternatively, copolymers may be periodic copolymers wherein units of the copolymer are arranged in repeating sequence (e.g., -X-X-Y-(X-X-Y-)$_n$ . . . , -X-Y-Z-Z-Y-(X-Y-Z-Z-Y-)$_n$ . . . , -(X-Y-X-Y-Y-X-X-X-X-Y-Y-Y-)$_n$ . . . , etc.). Periodic copolymers may be block copolymers wherein the constituent units within a species tend to be bound to another member of the same species (e.g., -(X-X-X-X-X-X-)$_n$-(Y-Y-Y-Y-Y-Y-)$_n$ . . . ). Copolymers may be statistical copolymers in which the sequence of constituent units follows a statistical rule, e.g., random copolymer (e.g., copolymer where any position along the copolymer chain has an equal probability of being occupied by monomer X or monomer Y proportional to the relative amounts of monomer X and Y in the whole polymer), gradient copolymer (e.g., a copolymer where the probability of monomer X occupying a particular position of the copolymer increases or decreases towards opposite ends of the copolymer), and the like. The number of species of constituent units that make up a heteropolymer varies and can be any number, e.g., in some cases the number of species may range from 2-20, e.g., from 2 to 10, from 2 to 5, from 2 to 4, from 4 to 10, or from 3 to 7.

Heteropolymers or copolymers may be "linear", i.e., heteropolymers or copolymers that consist of a single main chain or "branched", i.e., heteropolymers or copolymers that consist of at least two chains, e.g., a single main chain and at least one side chain. The number of side chains that make up a branched copolymer varies and can be any number and, e.g., in some cases may range from 1-20, e.g., from 1 to 10, from 1 to 5, from 1 to 3, from 2 to 4, from 4 to 10, or from 3 to 7.

As used herein the term "branched copolymer" may refer to a copolymer that contains two different homopolymers, e.g., a main chain homopolymer of monomer X and at least one side chain homopolymer of monomer Y. The term may also refer to a copolymer that contains a main chain homopolymer and at least one side chain heteropolymer, e.g., a main chain homopolymer of monomer X and at least one side chain heteropolymer of monomers Y and Z. The term may also refer to a copolymer that contains a main chain heteropolymer and at least one side chain homopolymer, e.g., a main chain heteropolymer of monomers Y and Z and at least one side chain homopolymer of monomer X. In some instances a monomer species may be present in both the main chain polymer and the side chain polymer, e.g., a main chain homopolymer of monomer X and at least one side chain heteropolymer of monomers X and Y or a main chain heteropolymer of monomers X and Y and at least one side chain homopolymer of monomer X. As such, branched heteropolymers or copolymers of the present disclosure may be graft copolymers, i.e. branched copolymers in which the side chains are structurally distinct from the main chain.

As used herein the term "branched copolymers" also may refer to special branched copolymers or combinations of special branched copolymers or combinations of non-special branched copolymers and special branched copolymers. Non-limiting examples of special branched copolymers include star copolymers, brush copolymers, comb copolymers, diblock copolymers, triblock copolymers, junction block copolymers, terpolymers, and the like.

As used herein the term "copolymer" may also refer to "stereoblock copolymers" or copolymers where a special structure is formed from repeating monomers such that blocks are defined by the tacticity of each block. Stereoblock copolymers include those copolymers that contain blocks of diads (e.g., meso diads and racemo diads), triads (e.g., isotactic triads, syndiotactic triads, and heterotactic triads), tetrads, pentads, and the like. For example, in certain embodiments, stereoblock copolymers may be or may include "eutactic polymers", i.e. polymers consisting of eutactic macromolecules where the substituents of the eutactic macromolecules are arranged in a sequence or pattern along the polymer backbone. Examples of eutactic polymers include, but are not limited to, isotactic polymers, syndiotactic polymers, and the like. For example, in certain embodiments, stereoblock copolymers may be or may include "isotactic polymers", i.e., polymers consisting of meso diads and containing isotactic macromolecules where the substituents of the macromolecules are all located on the same side of the macromolecular backbone. In certain embodiments, stereoblock copolymers of the present disclosure may be or may include "syndiotactic" or "syntactic polymers", i.e., polymers consisting of racemo diads and containing syndiotactic macromolecules where the substituents of the macromolecules alternate positions along the backbone chain.

As used herein the term "stereoblock copolymers" may also refer to or may also include "atactic polymers", i.e., polymers consisting of between 1 and 99 number percent meso diads and containing atactic macromolecules where the substituents of the atactic macromolecules are distributed randomly along the backbone chain.

Definitions related to polymers, or the assembly of polymers, of the present disclosure are taken to be those definitions commonly known to one skilled in the art. Such definitions may be found, e.g., in Whelan T. (1994) *Polymer technology dictionary*. London: Chapman & Hall, the disclosure of which is herein incorporated, in its entirety, by reference.

DETAILED DESCRIPTION

Spin columns that include a poly(acid) membrane separation matrix are provided. Also provided are kits that include the subject devices, as well as methods of using the devices, e.g., in sample preparation (such as protein purification) protocols.

Before the methods and kits of the present disclosure are described in greater detail, it is to be understood that the methods and kits are not limited to particular embodiments described, as such may, of course, vary. It is also to be understood that the terminology used herein is for the purpose of describing particular embodiments only, and is not intended to be limiting, since the scope of the methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and kits. The upper and lower limits of these smaller ranges may independently be included in the smaller ranges and are also encompassed within the methods and kits, subject to any specifically excluded limit in the stated range. Where the stated range includes one or both of the limits, ranges excluding either or both of those included limits are also included in the methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods and kits similar or equivalent to those described herein can also be used in the practice or testing of the methods and kits, representative illustrative methods and materials are now described.

All publications and patents cited in this specification are herein incorporated by reference as if each individual publication or patent were specifically and individually indicated to be incorporated by reference and are herein incorporated by reference to disclose and describe the methods, kits and/or materials in connection with which the publications are cited. The citation of any publication is for its disclosure prior to the filing date and should not be construed as an admission that the present methods and kits are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and kits, which are, for clarity, described in the context of separate embodiments, may also be provided in combination in a single embodiment. Conversely, various features of the methods and kits, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods and kits. Any recited method can be carried out in the order of events recited or in any other order which is logically possible.

Spin Columns

As summarized above, aspects of the invention include spin columns configured to separate components of a complex sample. Aspects of the spin columns include an elongated hollow structure having a sample inlet at a first end and a sample outlet at a second end; and a poly(acid) membrane matrix positioned in the elongated hollow structure such that fluid must flow through the poly(acid) membrane to traverse the structure from the first end to the second end.

The poly(acid) membrane matrix may vary. In some instances, the poly(acid) membrane matrix Includes a poly(acid) component adsorbed to a surface of a porous membrane support. The poly(acid) component may have a variety of configurations on the surface of the porous membrane component. For example, the poly(acid) component may be arranged as a film, e.g., coating or layer (including layer by layer) configuration on the surface of the porous membrane. Alternatively, the poly(acid) component may be configured as a plurality of polymeric brushes on a surface of the porous membrane. The surface of the porous membrane may be any surface, including an upper surface, the surface of the pores of the membrane, etc., where in some instances all surfaces of the membrane may be stably associated with, e.g., adsorbed to, the poly(acid) component.

Configurations of poly(acid) components configured as films may vary. For example, in some instances poly(acid) films configured in a coating configuration may be configured in a homopolymer coating. Homopolymer coating configurations are those poly(acid) films that may be composed of homopolymers, i.e., polymers derived from a single species of constituent unit. Homopolymer coatings also include those poly(acid) films that may be composed of a single species of heteropolymer or copolymer, i.e., a homo-heteropolymer coating.

In certain embodiments, poly(acid) films configured in a layer-by-layer configuration may be configured in a heteropolymer coating or a heteropolymer layer-by-layer configuration. Heteropolymer layer-by-layer configurations are those poly(acid) films that may be composed of two or more different heteropolymers. Heteropolymer layer-by-layer configurations also include those poly(acid) films that may be composed of at least two different species of homopolymers, i.e., a hetero-homopolymer.

Configurations of poly(acid) components configured as a plurality of polymeric brushes, i.e. poly(acid) polymeric brushes, may vary. For example, poly(acid) polymeric brushes may be configured in a homopolymer brush structure or a heteropolymer or copolymer brush structure. Homopolymer brush structures are those poly(acid) polymeric brushes that may be composed of a homopolymer. Homopolymer brush structures also include those poly(acid) polymeric brushes that may be composed of a single species of heteropolymer or copolymer, i.e., a homo-heteropolymer brush structure. Heteropolymer brush structures also includes those poly(acid) polymeric brushes that may be composed of at least two different species of homopolymers, i.e., a hetero-homopolymer brush structure.

The poly(acid) components of interest may include poly (acid) films and/or poly(acid) brushes composed of any convenient homopolymer or copolymer. Homopolymer and copolymer configurations may vary. Synthesis of homopolymers and copolymers may be controlled to produce any desired sequence or pattern of polymer blocks in order to produce a particular homopolymer or copolymer for use in the poly(acid) component.

Desired sequence or pattern of polymer blocks, whether unit blocks, e.g., in copolymers, or structural blocks, e.g., stereoblock polymers, may be achieved by any convenient method of polymer synthesis or assembly as described in, e.g., Braun et al. (2013) *Polymer Synthesis: Theory and Practice.* 5$^{th}$ ed. Springer, Ciferri A. (2005) *Supramolecular Polymers,* 2$^{nd}$ ed. CRC Press: Boca Raton, Fla., the disclosures of which are herein incorporated by reference. For example, in certain embodiments, desired sequence or pattern of polymer blocks may be achieved by the joining of unit blocks or structural blocks in a head to tail configuration. In certain embodiments, a desired sequence or pattern of polymer blocks may be achieved by the joining of unit blocks or structural blocks in a head to head configuration. In certain embodiments, a desired sequence or pattern of polymer blocks may be achieved by the joining of unit blocks or structural blocks in a tail to tail configuration.

Poly(acid) films may include those poly(acid) films synthesized by any convenient method. Methods useful in the synthesis of poly(acid) films vary but may include methods of adsorption of one or more polyelectrolytes (i.e., a homopolymer or copolymer with charged groups) onto a solid substrate, e.g., through the attachment of a polyelectrolyte to a substrate by means of electrical charge differences between the polyelectrolyte and the substrate. Methods useful in the synthesis of poly(acid) films may also include the subsequent attachment of a second polyelectrolyte to a first polyelectrolyte by means of a difference in electrical charge between the first and second polyelectrolytes. In certain instances, the attachment of the second polyelectrolyte to the first polyelectrolyte takes place after the first polyelectrolyte has attached to the substrate. In some embodiments, poly(acid) films may be composed of a single polyelectrolyte. In certain embodiments, poly(acid) films may be composed of two or more different polyelectrolytes, including e.g., 3 or more, 4 or more, 5 or more, 6 or more, 7 or more, 8 or more, 9 or more, or 10 or more.

Polyelectrolytes that find use in poly(acid) films may vary widely. For example, in some instances, such polyelectrolytes may represent anionic polyelectrolytes or polyanions, i.e., polyelectrolytes having a more negative charge as compared to the substrate or adjacent polyelectrolyte to which it is attached. In some instances, such polyelectrolytes may represent cationic polyelectrolytes or polycations, i.e., polyelectrolytes having a more negative charge as compared to the substrate or adjacent polyelectrolyte to which it is attached. As the charge of a particular polyelectrolyte may be dependent on characteristics of the solution in which the polyelectrolyte is dissolved, e.g., pH, a particular polyelectrolyte may be present as a polyanion or a polycation in different solutions, e.g., in solutions of different pH. As such, in certain instances, a polyelectrolyte may also be defined as a weak polyelectrolyte, e.g., having a pKa or pKb in the range of 2 to 10, or a strong polyelectrolyte, e.g., having a pKa or pKb outside the range of 2 to 10.

Anionic polyelectrolytes that find use in poly(acid) films include, but are not limited to, those available from commercial suppliers. For example, in certain embodiments, anionic polyelectrolytes are those available from Sigma-Aldrich (St. Louis, Mo.), such as poly(2-acrylamido-2-methyl-1-propanesulfonic acid), poly(2-acrylamido-2-methyl-1-propanesulfonic acid-co-acrylonitrile), poly (acrylic acid), polyanetholesulfonic acid, poly(sodium 4-styrenesulfonate), poly(4-styrenesulfonic acid), poly(4-styrenesulfonic acid-co-maleic acid), poly(vinyl sulfate), poly(vinylsulfonic acid), 4-styrenesulfonic acid, poly-L-glutamic acid, salts thereof and the like.

Cationic polyelectrolytes that find use in poly(acid) films include, but are not limited to, those available from commercial suppliers. For example, in certain embodiments, cationic polyelectrolytes are those available from Sigma-Aldrich (St. Louis, Mo.), such as poly(allylamine hydrochloride), poly(diallyldimethylammonium chloride), diallyldimethylammonium, poly(acrylamide-co-diallyldimethylammonium chloride), poly(2-dimethylamino)ethyl methacrylate), polyethylenimine, poly-L-glutamic acid, 8-anilino-1-naphthalenesulfonic acid, salts thereof and the like.

In certain embodiments, poly(acid) films derived from an anionic polyelectrolyte, e.g., poly(acrylic acid) (PAA), are adsorbed onto a substrate, e.g., a porous support, at low pH, e.g., at pH between 2 to 5, e.g., from pH 3 to 5, e.g., pH 3, pH 4, or pH 4.7. In certain embodiments an anionic polyelectrolyte is adsorbed directly to a substrate, e.g., PAA may be adsorbed directly to a porous membrane support. In some embodiments, an anionic polyelectrolyte is absorbed indirectly to a substrate, e.g., by means of an adhesion layer, e.g., PAA may be adsorbed to an adhesion layer that is adsorbed to a porous membrane support. Any convenient agent that attaches to a substrate to facilitate the subsequent attachment of a polyanion or polycation may find use as an adhesion layer. In some instances, agents that find use in adhesion layers may be those agents that form multiple hydrophobic interactions with a porous membrane support. Adhesion layer agents may vary widely but in some cases may include poly(styrene sulfonate) (PSS).

In certain embodiments, layer-by-layer configurations of poly(acid) films may include those poly(acid) films where an adhesion layer containing one or more adhesion layer agents, e.g., PSS, is first layered on a porous support. In certain embodiments, layer-by-layer configurations of poly (acid) films may include those poly(acid) films where one or more anionic polyelectrolytes, e.g., PAA, are first layered on a porous support, e.g., without the use of an adhesion layer. In certain embodiments, after the layering of one or more anionic polyelectrolytes, one or more cationic polyelectrolytes, e.g., protonated poly(allyl amine) (PAH), polyethyleneimine (PEI), etc., are layered on the anionic polyelectrolyte. In certain embodiments, a combination of two more polyelectrolytes are layered on a porous support, e.g., a combination of PAH and PAA or a combination of PEI and PAA, with or without the use of an adhesion layer. Accordingly, poly(acid) films may be simple or may be complex. Simple poly(acid) films will vary but may include those poly(acid) films that include a small number of poly electrolyte layers, e.g., one layer, two layers, or three layers. Complex poly(acid) films will vary but may include those poly(acid) films that include more than a small number of polyelectrolyte layers, e.g., 3 or more layers, e.g., 4 or more layers, 5 or more layers, 6 or more layers, 7 or more layers, 10 or more layers, 15 or more layers, or 20 or more layers. Any desired number or combination of layers may be constructed in the resulting poly(acid) film.

Poly(acid) polymeric brushes may include those poly (acid) polymeric brushes synthesized by any convenient method. For example, methods useful in the synthesis of poly(acid) polymer brushes include, but are not limited to: plasma polymerization, heat-assisted or UV-assisted graft polymerization, nitroxide-mediated polymerization, reversible addition-fragmentation chain-transfer polymerization, atom-transfer radical polymerization (ATRP), surface-initiated ATRP, and the like. Any particular method may be utilized, or parts of methods may be combined or exchanged, in order to achieve desired reaction characteristics. Such desired reaction characteristics may vary. For example, in some embodiments, desired reaction characteristics include, but are not limited to, polymerization in aqueous solution (e.g., polymerization in a solution that is not an organic solvent), minimized in solution polymerization (i.e., a high preference for polymerization of substrate bound polymers over non-substrate bound polymers), controlled polymer growth rate, efficient polymer growth, and low polydispersities (i.e. a small range of polymer sizes).

In certain embodiments, the poly(acid) polymeric brushes may be those synthesized by surface initiated ATRP, where ATRP is initiated through the attachment of an initiator to a substrate. In certain embodiments the substrate to which the initiator is attached may be the porous membrane support. In other embodiments, the substrate to which the initiator is attached may be an intermediate substrate upon which ATRP is initiated before, during, or after the intermediate substrate is attached to the porous membrane support. For example, in certain embodiments, the initiator is attached to an intermediate substrate, e.g., a polymer primer, after the intermediate substrate is attached to the porous support.

Intermediate substrates useful in mediating attachment of an ATRP initiator to a porous support may vary widely. Such intermediate substrates are those substrates that attach simultaneously to a primary substrate, e.g., a porous support, and to a component of a polymer, e.g., an initiator or a monomer. In some instances, an intermediate substrate may be a polymer. In certain instances adhesion layer agents may find use as intermediate substrates, e.g., PSS may be used as an intermediate substrate.

Initiators may vary and may be any convenient initiator capable of initiating polymerization, e.g., radical polymerization, e.g., ATRP. Polymerization initiators of interest include, but are not limited to, those available from commercial suppliers, e.g., Sigma-Aldrich (St. Louis, Mo.). Initiators of radical polymerization include, but are not limited to, those radical polymerization initiators disclosed in Denisov et al. (2005) *Free Radical Initiators*. John Wiley & Sons: New Jersey, the disclosure of which is herein incorporated by reference. In certain embodiments, radical polymerization initiators may also include silane initiators, e.g., trichlorosilane.

Examples of ATRP initiators that may find use in constructing poly(acid) components include, but are not limited to: bis[2-(2'-bromoisobutyryloxy)ethyl]disulfide, bis[2-(2-bromoisobutyryloxy)undecyl]disulfide, 2-bromoisobutyric anhydride, α-bromoisobutyryl bromide, 2-(2-bromoisobutyryloxy)ethyl acrylate, 2-(2-bromoisobutyryloxy)ethyl methacrylate, tert-butyl α-bromoisobutyrate, 3-butynyl 2-bromoisobutyrate, dipentaerythritol hexakis(2-bromoisobutyrate), dodecyl 2-bromoisobutyrate, ethyl α-bromoisobutyrate, ethylene bis(2-bromoisobutyrate), 2-hydroxyethyl 2-bromoisobutyrate, 1-(DL-1,2-isopropylideneglyceryl) 2-bromoisobutyrate, methyl α-bromoisobutyrate, octadecyl 2-bromoisobutyrate, pentaerythritol tetrakis(2-bromoisobutyrate), 1-(phthalimidomethyl) 2-bromoisobutyrate, poly(ethylene glycol) bis(2-bromoisobutyrate), poly(ethylene glycol) methyl ether 2-bromoisobutyrate, propargyl 2-bromoisobutyrate, 1,1,1-tris(2-bromoisobutyryloxymethyl)ethane 10-Undecenyl 2-bromoisobutyrate, and the like.

In certain embodiments an initiator is further bound to one or more units of a polymer, e.g., a unit block, a monomer, or a macromonomer, in order to form a macroinitiator. Methods of constructing macroinitiators vary and in some cases a polymer may be post-polymerization modified with an initiator, e.g., an ATRP initiator, or in other cases a polymer may be copolymerized with an initiator, e.g., an ATRP initiator. Any convenient unit of a polymer may find use as an incorporation site of an initiator in order to from a macroinitiator. Suitable initiators may be incorporated into a macroinitiator at any desired number percentage of a formed polymer where higher percentages of initiator incorporation result in higher rates of subsequent polymerization, e.g., higher polymer density, and lower percentages of initiator incorporation result in lower rates of subsequent polymerization, e.g., a lower polymer density. For example, in some instances initiators, e.g., ATRP initiators, may be present at anywhere from 1 to 50% in the macroinitiator, e.g., from 1 to 30%, from 10 to 40%, from 10 to 30%, from 1 to 20%, from 15 to 25%, or from 10 to 20%.

In certain instances, a macroinitiator may include an initiator bound to a cationic and anionic polymer, e.g., a cationic polyelectrolyte or anionic polyelectrolyte. For example, a macroinitiator may include an initiator, e.g., 2-(2-bromoisobutyryloxy)ethyl acrylate (BIEA), bound to a cationic polymer, e.g., 2-dimethylamino)ethyl methacrylate (DMAEMA). In some instances, a macroinitiator is further modified to improve reactivity, e.g., an macroinitiator may be further modified, e.g., alkylated with an alkylating agent, e.g., methylated with a methylating agent, in order to form a modified macroinitiator, e.g., poly(DMAEMA-co-BIEA) may be alkylated with methyl iodide to generate the modified macroinitiator poly(2-trimethylammonium iodide)ethyl methacrylate-co-BIEA) (TMAEMA-co-BIEA). In some instances, a macroinitiator or modified macroinitiator of a poly(acid) component is directly attached to the porous support. In other instances, a macroinitiator or modified macroinitiator is attached to a porous sport through the use of an intervening layer or substrate, e.g., an adhesion layer or an intermediate substrate.

Poly(acid) layers and brushes finding use in embodiments of the invention include, but are not limited to, those described in: Jain et al., "Protein Purification with Polymeric Affinity Membranes Containing Functionalized Poly(acid) Brushes," Biomacromolecules (Apr. 12, 2010): 11:1019-1026; Anuraj et al., "An All Aqueous Route to Polymer Brush-Modified Membranes with Remarkable Permeabilities and Protein Capture Rates," J. Memb. Sci. (Feb. 1, 2012) 389: 117-125; Bhattacharjee et al., "Formation of High-Capacity Protein-Adsorbing Membranes Through Simple Adsorption of Poly(acrylic acid)-Containing Films at Low pH," Langmuir (May 1, 2012): 28: 6885-6892; Jain et al., "Completely Aqueous Procedure for the Growth of Polymer Brushes on Polymeric Substrates," Langmuir (2007) 23:11360-11365; the disclosures of which are herein incorporated by reference. Also of interest are the poly(acid) membranes published in United States Published Application No. 20130244338; the disclosure of which is herein incorporated by reference.

In addition to the poly(acid) component, the matrix further includes a porous membrane support. The porosity of the membrane may vary as desired. For example, in embodiments where high flow rate through the membrane is desired a membrane with high porosity may be used or in embodiments where membrane rigidity is desired a membrane with low porosity may be used. The average pore size of the pores of the membrane may also vary as desired and may range from, e.g., from 0.2 to 20 µm in diameter, including e.g., from 0.2 to 0.4 µm, from 0.2 to 0.5 µm, from 0.3 to 0.5 µm, from 0.3 to 0.6 µm, from 0.2 to 1 µm, from 0.5 to 1 µm, 0.7 to 1.5 µm, 0.9 to 1.3 µm, from 1 to 10 µm, from 1 to 5 µm, from 1 to 3 µm, from 1 to 2 µm, from 2 to 5 µm, from 2 to 4 µm, from 3 to 5 µm, or from 4 to 5 µm. In some instances, average pore size of a membrane may be chosen based on the size of the poly(acid) component adhered to the membrane. For example, where a smaller poly(acid) component, e.g., a small poly(acid) film, is adhered to a membrane with a smaller average pore size, e.g., from 1 to 2 µm in diameter, including e.g., 1.2 µm, may be used. In other instances where a larger poly(acid) component, e.g., a large poly(acid) brush, is adhered a membrane with a larger average pore size, e.g., from 3 to 6 µm in diameter, including e.g., 5 µm, may be used. The use of a large poly(acid) component may or may not require the use of a membrane with large average pore size. For example, in some instances, a large poly(acid) component may be used in conjunction with a membrane of small average pore size. Likewise, in some instances, a small poly(acid) component may be used in conjunction with a membrane of large average pore size.

Average pore size refers to the arithmetic mean of the size of the pores of a membrane. Any convenient standard measurement of pore size, e.g., pore diameter or pore volume, may be used in calculating average pore size. In some instances, average pore size may also be determined by directly measuring the size of a representative sample or a representative number of pores and one need not measure every pore of a membrane in order to determine the average pore size of a membrane. In some instances, average pore size may be determined indirectly by measuring a functional characteristic of a subject membrane and estimating pore size based on measurements of the same functional characteristic measured in a reference membrane of known average pore size. These indirect methods must also consider, and in some cases measure, the pore distribution or pore density in order to accurately determine average pore size. Pore size and pore distribution may be measured by any convenient method including, but not limited to: the bubble point method, mercury porosimetry, thermoporometry, permporometry, the absorption method, methods based on liquid or gas transport, microscopic methods (e.g., light microscopy, scanning electron microscopy, transmission electron microscopy, atomic force microscopy, etc.). Such methods include, but are not limited to; those described and reviewed in Khulbe et al. (2008) *Synthetic polymeric membranes: characterization by atomic force microscopy*. Berlin: Springer, the disclosure of which is incorporated herein by reference.

The porous membrane support may be made up of a variety of materials, including but not limited to: polymeric materials, e.g., nylons, plastics, etc. In certain embodiments polyamides may be used as the porous membrane support. Polyamides useful as membranes of the present disclosure may vary and may be either natural occurring or synthetic. In certain embodiments, the polyamide membrane is a nylon membrane. Nylon membranes may be either hydroxylated or non-hydroxylated. In certain instances, surface groups, e.g., surface amide groups, of non-hydroxylated membranes, e.g., non-hydroxylated nylon membranes, may be activated by conversion to active surface groups to form a hydroxyl-functionalized membrane, e.g., conversion of surface amide groups on non-hydroxylated nylon membranes to N-methylol polyamide (nylon-OH) surface groups. Any convenient material may be used in the porous membrane support, including such non-limiting examples as: sulfone containing polymers, e.g., polysulfone, polyethersulfone, and the like; fluoropolymers, e.g., polyvinylidene fluoride and the like; cellulose polymers; and the like. As described herein materials of the porous membrane support are not limited to those materials which are stable in organic solvents, e.g., materials that normally dissolve or disassociate in organic solvents may also be used in the porous membrane support through the use of aqueous assembly.

Where desired, the poly(acid) matrix may further include an affinity element. The affinity element is an element or component that displays binding affinity for a category of molecules or a specific molecule. Affinity elements may be, in some cases defined as non-specific affinity elements, e.g., those affinity elements that bind a category of molecules, or, in some instances, may be defined as specific affinity elements, e.g., those affinity elements that bind a specific molecule.

In some instances, the affinity element is a non-specific affinity element, such as a metal ion chelating ligand complexed with a metal ion which, e.g., which binds to any suitable tagged protein in a given sample. The metal ion chelating ligand complexed with a metal ion may vary with respect to the ligand and the metal ion. Examples of ligands of interest include, but are not limited to: iminodiacetic acid (IDA), nitriloacetic acid (NTA), caboxymethylated aspartic acid (CM-Asp), tris(2-aminoethyl) amine (TREN), and tris-carboxymethyl ethylene diamine (TED). These ligands offer a maximum of tri-(IDA), tetra-(NTA, CM-Asp), and pentadentate (TED) complexes with the respective metal ion. A variety of different types of metal ions may be complexed to the ligands of the subject compounds. Metal ions of interest can be divided into different categories (e.g., hard, intermediate and soft) based on their preferential reactivity towards nucleophiles. Hard metal ions of interest include, but are not limited to: $Fe^{3+}$, $Ca^{2+}$ and $Al^{3+}$ and like. Soft metal ions of interest include, but are not limited to: $Cu^+$, $Hg^{2+}$, $Ag^+$, and the like. Intermediate metal ions of interest include, but are not limited to: $Cu^{2+}$, $Ni^{2+}$, $Zn^{2+}$, $Co^{2+}$ and the like. In certain embodiments, the metal ion that is chelated by the ligand is $Co^{2+}$. In certain embodiments, the metal ion of interest that is chelated by the ligand is $Fe^{3+}$. Additional metal ions of interest include, but are not limited to lanthanides, such as $Eu^{3+}$, $La^{3+}$, $Tb^{3+}$, $Yb^{3+}$, and the like.

In certain embodiments, the affinity element includes aspartate groups and is referred to as an aspartate-based metal ion affinity element, where such compositions include a structure that is synthesized from an aspartic acid, e.g., L-aspartic acid. Aspartate-based metal ion affinity elements include aspartate-based ligand/metal ion complexes, e.g., tetradentate aspartate-based ligand/metal ion complexes, where the metal ion complexes have affinity for proteins, e.g., proteins tagged with a metal ion affinity peptide. In some instances, aspartate-based compositions of the present disclosure include structures having four ligands capable of interacting with, i.e., chelating, a metal ion, such that the metal ion is stably but reversibly associated with the ligand, depending upon the environmental conditions of the ligand.

In certain embodiments, non-specific affinity elements include tag-binding affinity elements that directly bind a protein tag, e.g., an epitope tag, or a substrate tag, e.g., a chemical tag. The tag-binding affinity element may vary with respect to the tag.

For example, in some instances, the tag may be a polypeptide epitope tag, e.g., a FLAG epitope, and the tag-binding affinity element may be a polypeptide, e.g., an antibody, that directly binds the polypeptide epitope tag, e.g., an anti-FLAG antibody. Antibodies that bind polypeptide epitope tags include but are not limited to: anti-FLAG antibodies, anti-His epitope tag antibodies, anti-HA tag antibodies, anti-Myc epitope tag antibodies, anti-GST tag antibodies, anti-GFP tag antibodies, anti-V5 epitope tag antibodies, anti-6×His tag antibodies, anti-6×HN tag antibodies, and the like. Such antibodies are available from commercial suppliers, e.g., from Clontech (Mountain View, Calif.), Thermo Scientific (Rockford, Ill.), and the like.

In other instances, the tag may be a chemical substrate that directly binds with a binding partner. The chemical substrate may be any convenient chemical substrate with one or more binding partners. For example, the chemical substrate may be biotin and thus the tag-binding affinity element may be any binding partner of biotin, e.g., avidin, streptavidin, an anti-biotin antibody, and the like. Further examples of tag-binding affinity elements that bind chemical substrates include, but are not limited to, anti-horseradish peroxidase antibodies, anti-digoxigenin antibodies, anti-alkaline phosphatase antibodies, anti-fluorescein isothiocyanate antibodies, anti-tetramethylrhodamine antibodies, and the like. Such tag-binding affinity elements are available from commercial suppliers, e.g., from Thermo Scientific (Rockford, Ill.), Life Technologies (Carlsbad, Calif.), Sigma-Aldrich (St. Louis, Mo.), and the like.

In some instances, the affinity element is a specific affinity element. Specific affinity elements are those elements that have a specific affinity for an analyte of interest. Specific affinity elements may vary, where examples of such elements include, but are not limited to: antibodies, e.g., monoclonal or polyclonal antibodies, or binding fragments thereof. Specific affinity elements specifically exclude those affinity elements that bind commonly used tags, e.g., protein epitope tags, and are therefore distinct from non-specific affinity elements as described herein. Methods of developing and using specific affinity elements are described in, e.g., Harlow & Lane (1999) *Using Antibodies: A laboratory manual*. Cold Spring Harbor Press: Cold Spring Harbor, N.Y. and Shepherd & Dean (2000) *Monoclonal antibodies—practical approach*. Oxford University Press: Oxford, UK, the disclosures of which are herein incorporated by reference.

The poly(acid) matrix of the column may be made up of a single membrane or two or more distinct membranes, e.g., stacked on top of each other, such as three or more, four or more, five or more membranes, as desired. In certain embodiments, stacked membranes may be separated by spacers. The configuration of membrane spacers may vary widely and include, but are not limited to: hollow spacers, solid spacer, porous spacers, liquid spacers, gel spacers, fibrous spacers, polymeric spacers, and the like. The dimensions of the poly(acid) matrix may vary, where the matrix may be configured to occupy a portion of the volume of the spin column and such portion may vary, ranging from 0.1% to 100%, including e.g., 0.1% to 0.5%, 0.1% to 0.3%, 0.2% to 0.3%, 0.1% to 1%, 0.1% to 10%, 1% to 10%, 1% to 50%, 5% to 100%, 10% to 100%, 25% to 100%, 50% to 100%, 75% to 100%, and including the total volume of the spin column. Where the poly(acid) matrix occupies only a portion of the volume of the spin column, it may be positioned at any desired location, such as a location in the middle or proximal to one of the ends, such as the second end where the sample outlet is located.

In addition to the poly(acid) matrix, the spin column includes an elongated hollow structure having a sample inlet at a first end and a sample outlet at a second end. The structure may have any desired configuration, where in some instances the structure is configured as a tube. The volume of the structure may vary, where in some instances the elongated structure has a volume of 1 µl or more, such as 5µ or more, including 10, 25, 50 or 75 µl or more, where in some instances the volume is 1 ml or more, such as 5 ml or more, including 10, 25, 50, 100, 250, 500, 750 ml or more, up to 1l or more, where in some instances the volume ranges from 1 µl to 1l.

As mentioned above, the elongated structure includes a sample inlet at a first end and a sample outlet at a second end. The dimensions of each of the inlet and outlet may be the same or different, where in some instances the longest dimension, e.g., diameter, of the inlet is longer than that of the outlet, e.g., by 5, 10, 15, 20, 25, 50, 75, or 100% or more.

The elongated structure may be fabricated from any convenient material, including but not limited to polymeric materials, e.g., plastics, where the material may be opaque or transparent, as desired. Useful materials in fabricating the elongated structure include, but are not limited to, those polymeric materials, e.g., plastics, resins, etc., that are commonly used in research and industrial settings, including but not limited to: acetal, cyclic olefin copolymer, ethylene propylene diene monomer rubber, ethylene propylene rubber, ethylene-chlorotrifluoroethylene copolymer (Halar®), ethylene-tetrafluoroethylene (Tefzel), fluorinated ethylene propylene (Teflon®), fluorinated polyethylene, high impact polystyrene, high-density polyethylene, low-density polyethylene, modified polyphenylene ether, Permanox, polycarbonate, polyetherimide, polyethylene teraphthalate, polyethylene terephthalate copolymer, polyfluoroalkoxy (Teflon®), polymethyl methacrylate (acrylic), polymethylpentene, polypropylene, polypropylene copolymer, polystyrene, polysulfone, polyvinylidenedifluoride, ResMer™, styrene acrylonitrile, tetrafluoroethylene, tetrafluoroethylene (Teflon®), Thermanox, thermoplastic elastomer, thermoplastic polyester polyurethane, Tritan™, and the like.

The dimensions of the elongated structure may vary widely and can be chosen based on a variety of factors. For example, in certain embodiments, the dimensions of the elongated structure may be chosen based on the maximum binding capacity of the poly(acid) matrix that is subsequently affixed within the elongated structure. In some instances the dimensions of the elongated structure provide for the loading of a sample of a certain volume such that the likely amount of the target protein in the sample nearly equals, e.g., is within 98% of, is within 95% of, is within 90% of, the maximum binding capacity of the poly(acid) matrix. In certain instances the dimensions of the elongated structure provide for the loading of a sample of a certain volume such that the likely amount of the target protein in the sample exceeds, e.g., is 1.5 times greater than, is 2 times greater than, is 3 times greater than, is 5 times greater than, is 10 times greater than, the maximum binding capacity of the poly(acid) matrix. In yet other embodiments, the dimensions of the elongated structure provide for the loading of a sample of a certain volume such that the likely amount of the target protein in the sample is less than, e.g., is 1.5 times less than, is 2 times less than, is 3 times less than, is 5 times less than, is 10 times less than, the maximum binding capacity of the poly(acid) matrix.

The dimensions of the elongated structure may be scaled according to the desired application scale of protein production. For example, the dimensions of the elongated structure may be scaled such that they are sufficient to enclose both a sufficient amount of space for the application of a sample containing research scale protein amounts and a sufficient amount of poly(acid) matrix for isolating research scale protein amounts, e.g., nanogram amounts, e.g., 0.5 ng to 500 ng.

In certain embodiments, the dimensions of the elongated structure may be scaled such that they are sufficient to enclose both a sufficient amount of space for the application of a sample containing screening scale protein amounts and a sufficient amount of poly(acid) matrix for isolating screening scale protein amounts, e.g., microgram amounts, e.g., 0.5 µg to 500 µg.

In certain embodiments, the dimensions of the elongated structure may be scaled such that they are sufficient to enclose both a sufficient amount of space for the application of a sample containing batch scale protein amounts and a sufficient amount of poly(acid) matrix for isolating batch scale protein amounts, e.g., milligram amounts, e.g., 0.5 mg to 100 mg, including, e.g., 1 mg to 50 mg.

In certain embodiments, the dimensions of the elongated structure may be scaled such that they are sufficient to enclose both a sufficient amount of space for the application of a sample containing pilot scale protein amounts and a sufficient amount of poly(acid) matrix for isolating pilot scale protein amounts, e.g., milligram to gram amounts, e.g., 100 mg to 10 g, including, e.g., 500 mg to 5 g, and 1 g to 10 g.

In certain embodiments, the dimensions of the elongated structure may be scaled such that they are sufficient to enclose both a sufficient amount of space for the application of a sample containing process scale protein amounts and a sufficient amount of poly(acid) matrix for isolating process scale protein amounts, e.g., gram to kilogram amounts, e.g., 10 g to 1 kg, including, e.g., 50 g to 500 g, 100 g to 500 g, and 500 g to 1 kg.

The actual length and diameter dimensions of the elongated structures sufficient to enclose both a sufficient amount of space for the application of a sample and sufficient amount of poly(acid) matrix for isolating protein from the sample may vary greatly, e.g., from millimeters up to meters, considering the wide range of protein amounts that may be isolated using spin columns of the present disclosure. For example, the lengths of the elongated structures suitable for use in research scale, screening scale, batch scale, pilot scale, and process scale applications may and in some cases, range from 5 to 500 mm, e.g., mm to 40 mm, from 40 mm to 80 mm, from 80 mm to 110 mm, form 90 mm to 200 mm, and from 200 mm to 1 m, and the diameters may range from range from 3 mm to 15 mm, from 10 mm to 20 mm, from 15 mm to 30 mm, form 30 mm to 100 mm, and from 90 mm to 500 mm, respectively.

As disclosed elsewhere herein, in certain instances, the sample from which the protein is isolated or purified may be pre-concentrated, e.g., water, media, buffer, or other sample constituents may be removed from the sample, thus increasing the relative concentration of the target protein, prior to the sample being loaded into a device of the present disclosure. In certain instances, such concentration allows the loading of large amounts of protein, e.g., batch scale amounts, pilot scale amounts, process scale amounts, etc., into the elongated structure of described dimensions. In yet other embodiments, multiple applications of sample into the elongated structure of described dimensions may be used to isolate or purify large amounts of protein through the binding of large amounts of proteins, e.g., batch scale amounts, pilot scale amounts, process scale amounts, etc., to a poly(acid) matrix capable of binding such large amounts.

Actual configurations and dimensions of the elongated structure of the present disclosure may vary widely and may include, in some instances, an essentially cylindrical tube configured to be compatible with conventional laboratory or industrial centrifuges, e.g., configured to fit into conventional rotors of conventional laboratory or industrial centrifuges. Such rotors may be, e.g., those available from commercial suppliers such as Beckman Coulter (Indianapolis, Ind.), Eppendorf (Hamburg, Germany), Thermo Scientific (Rockford, Ill.), and the like. For example, such rotors may be those described in or similar to those described in the *Thermo Scientific Rotor Guide* (2011) available from Thermo Fisher Scientific (Rockford, Ill.), *High-Performance and High-Capacity Centrifuges* (2008) catalog available from Beckman Coulter (Indianapolis, Ind.), and the 2014/15 *Eppendorf Products Catalog: Liquid Handling, Sample Handling, and Cell Handling* available from Eppendorf (Hamburg, Germany), the disclosures of which are herein incorporated, in their entirety, by reference.

In certain embodiments, the elongated structure may be configured to be compatible with conventional rotors used to centrifuge small volumes, e.g., 2 mL or less, in centrifuges known in the art as micro centrifuges. For example, in some instances, the elongated structure may be configured to be compatible with a conventional rotor configured for 1.5 mL or 2.0 mL tubes, e.g., 40 mm long or shorter and 11 mm in diameter or less. In other embodiments, the elongated structure may be configured to be compatible with a conventional rotor or conventional rotor adaptor configured for 0.5 mL tubes, e.g., 30 mm or shorter and 8 mm in diameter or less.

In certain embodiments, the elongated structure may be configured to be compatible with conventional rotors used to centrifuge medium volumes, e.g., from 2 mL to 50 mL, in centrifuges known in the art as general purpose or multipurpose centrifuges. In some embodiments, the elongated structure may be configured to be compatible with a conventional rotor or conventional rotor adaptor configured for 5 mL tubes, e.g., 75 mm long or shorter and 12 mm in diameter or less. In some embodiments, the elongated structure may be configured to be compatible with a conventional rotor or conventional rotor adaptor configured for 13 mL or 14 mL tubes, e.g., 100 mm long or shorter and 18 mm in diameter or less. In some embodiments, the elongated structure may be configured to be compatible with a conventional rotor or conventional rotor adaptor configured for 15 mL tubes, e.g., 120 mm long or shorter and 17 mm in diameter or less. In some embodiments, the elongated structure may be configured to be compatible with a conventional rotor or conventional rotor adaptor configured for 50 mL tubes, e.g., 115 mm long or shorter and 30 mm in diameter or less.

In certain embodiments, the elongated structure may be configured to be compatible with conventional rotors used to centrifuge large volumes, e.g., greater than 50 mL, in centrifuges known in the art as large capacity centrifuges. General purpose or multipurpose centrifuges may also be configured to centrifuge large volumes. In some embodiments, the elongated structure may be configured to be compatible with a conventional rotor or conventional rotor adaptor configured for 85 or 100 mL bottles, e.g., 121 mm long or shorter and 38 mm in diameter or less. In some embodiments, the elongated structure may be configured to be compatible with a conventional rotor or conventional rotor adaptor configured for 225 mL or 250 mL bottles, e.g., 137 mm long or shorter and 62 mm in diameter or less. In some embodiments, the elongated structure may be configured to be compatible with a conventional rotor or conventional rotor adaptor configured for 400 or 500 mL bottles, e.g., 136 mm long or shorter and 98 mm in diameter or less. In some embodiments, the elongated structure may be configured to be compatible with a conventional rotor or conventional rotor adaptor configured for 750 mL bottles, e.g., 150 mm long or shorter and 104 mm in diameter or less. In some embodiments, the elongated structure may be configured to be compatible with a conventional rotor or conventional rotor adaptor configured for 1 L bottles, e.g., 189 mm long or shorter and 98 mm in diameter or less. In some embodiments, the elongated structure may be configured to be compatible with a conventional rotor or conventional rotor adaptor configured for 2 L bottles.

In certain embodiments the elongated structure is configured as an essentially cylindrical tube configured to be placed inside a collection tube. Collection tubes may vary and may be either specifically designed to be compatible with the elongated structure or may be any conventional laboratory tube that is compatible with the elongated structure. For example, conventional laboratory tubes, e.g., laboratory tubes configured to be compatible with a conventional laboratory or industrial centrifuge, include, but are not limited to, 0.5 mL microcentrifuge tubes, 1.5 mL microcentrifuge tubes, 2.0 mL microcentrifuge tubes, 5 mL centrifuge tubes, 13 mL centrifuge tubes, 15 mL centrifuge tubes, 50 mL centrifuge tubes. Such conventional laboratory or industrial centrifuge tubes include those that are commercially available, e.g., from Eppendorf (Hamburg, Germany), BD Biosciences (San Jose, Calif.), Thermo Fisher Scientific (Rockford, Ill.), and the like. For example, in some instances, the elongated structure may be configured to be compatible with a 2.0 mL collection tube, e.g., 9.8 mm in diameter or less, 39 mm in length or shorter (e.g., from 5 mm to 33 mm in length), and with or without a top lip of 9.9 mm in diameter or greater. In some instances, the elongated structure may be configured to be compatible with a 1.5 mL collection tube, e.g., 9.8 mm in diameter or less, 38 mm in length or shorter (e.g., from 5 mm to 20 mm in length), and with or without a top lip of 9.9 mm in diameter or greater. In some instances, the elongated structure may be configured to be compatible with a 0.5 mL collection tube, e.g., 6.7 mm in diameter or shorter, 29 mm in length or shorter (e.g., from 5 mm to 17 mm in length), and with or without a top lip of 6.7 mm in diameter or greater. In some instances, the elongated structure may be configured to be compatible with a 5 mL collection tube, e.g., 17 mm in diameter or less, 65 mm in length or shorter, and with or without a top lip of 17 mm in diameter or greater. In some instances, the elongated structure may be configured to be compatible with a 15 mL collection tube, e.g., 17 mm in diameter or less, 125 mm in length or shorter, and with or without a top lip of 17 mm in diameter or greater. In some instances, the elongated structure may be configured to be compatible with a 50 mL collection tube, e.g., 31 mm in diameter or less, 121 mm in length or shorter, and with or without a top lip of 31 mm in diameter or greater.

In certain embodiments the elongated structure is configured as an essentially cylindrical tube configured to be placed inside a collection bottle. Collection bottles may vary and may be either specifically designed to be compatible with the elongated structure or may be any conventional laboratory bottle that is compatible with the elongated structure. For example, conventional laboratory bottles, e.g., laboratory bottles configured to be compatible with a conventional laboratory or industrial centrifuge, include, but are not limited to, 100 mL bottles, 175-225 mL conical bottles, 250 mL flat bottom bottles, 400 mL bottles, 500 mL bottles, 750 mL bottles, 1 L bottles, 1.5 L bottles, 2 L bottles, and the like. Such conventional laboratory or industrial centrifuge bottles include, but are not limited to, those commercially available, e.g., from Eppendorf (Hamburg, Germany), BD Biosciences (San Jose, Calif.), Thermo Fisher Scientific (Rockford, Ill.), and the like.

In certain embodiments the elongated structure is configured as an essentially cylindrical tube configured to be placed inside a well of a multi-well plate. In some embodiments, the multi-well plate may be configured to receive an elongated structure configured to be placed into one of the tubes described above, e.g., a 0.5 mL collection tube, a 1.5 mL collection tube or a 2 mL collection tube. In other embodiments, the elongated structure is specially configured to be placed inside a well of a particular multi-well plate. Multi-well plates may vary and may be either specifically designed to be compatible with the elongated structure or may be any conventional laboratory multi-well plate that is compatible with the elongated structure. For example, conventional laboratory multi-well plates, e.g., laboratory multi-well plates configured to be compatible with a conventional laboratory or industrial centrifuge or centrifuge rotor or centrifuge rotor insert, include, but are not limited to 96-well plates, 384-well plates, 1536-well plates, and the like. Such conventional laboratory or industrial multi-well plates include those that are commercially available, e.g., from Sigma-Aldrich (St. Louis, Mo.), Eppendorf (Hamburg, Germany), BD Biosciences (San Jose, Calif.), Thermo Fisher Scientific (Rockford, Ill.), and the like. In some embodiments, a supplemental attachment, e.g., a holder, a jig, a coupling, etc., may be provided to maintain sufficient association of the elongated structure with a particular multi-well plate.

In certain embodiments the elongated structure may, for example, be or be configured as a commercially available tube or spin column. Such commercially available tubes and spin columns include those available from Thermo Scientific (Rockford, Ill.), Sigma-Aldrich (St. Louis, Mo.), G-Biosciences (St. Louis, Mo.), Pall Life Sciences (Ann Arbor, Mich.), GE Healthcare Life Sciences (Pittsburgh, Pa.), and the like.

For example, commercially available tubes and spin columns include, but are not limited to, those available from Thermo Scientific (Rockford, Ill.), e.g., those having snap caps (e.g., with dimensions of: 9 mm in diameter and 20 mm in height with a lip of greater than 9 mm in diameter, 9 mm in diameter and 24 mm in height with a lip of greater than 9 mm in diameter, 9 mm in diameter and 30 mm in height with a lip of greater than 9 mm in diameter, and the like), those having screw caps (e.g., with dimensions of: 8 mm in diameter and 32 mm in height, 4 mm in diameter and 37 mm in height, and the like), those having screw caps and twist-off bottoms (e.g., with dimensions of: 9 mm in diameter and 39 mm in height, 9 mm in diameter and 100 mm in height, 12 mm in diameter and 105 mm in height, 17 mm in diameter and 112 mm in height, and the like).

In certain embodiments, the elongated structure may also be configured for the attachment of an extender, such an extender allowing for the application of additional sample volume to the device that would otherwise exceed the maximum volume of the elongated structure. Such an extender may be held in place to the first sample inlet of the elongated structure by any convenient means, e.g., by friction forces, by tension forces or by adhesive, etc. The connection between the elongated structure and the extender may or may not be air-tight. For example, in instances when the extender is configured to allow for gravity-flow of sample into the elongated structure a non-air-tight connection may be used. In instances when the extender is configured to allow for pressure-flow, e.g., vacuum pressure flow or positive pressure flow, of sample into the elongated structure an air-tight connection may be desired. In some instances, the extender may also function as a pre-filter. For example, the extender may contain a filter of any convenient filter material, e.g., a paper filter, a glass fiber filter, a plastic filter, a gel filter, etc., that may retain some component of the sample in order to prevent the component from entering the elongated structure. In certain embodiments, flow, either passive or active, may be controlled by a flow control device positioned between the extender and the elongated structure, e.g., a valve or stopcock.

In some instances, the poly(acid) matrix may be supported in the elongated structure by a support member. The support member may vary greatly in structure, e.g., pins, cross bars, etc., where in some instances the support member is structured as a frit. The support member may or may not be readily removable from the elongated structure. Any suitable support material may find use as a support member. Examples of suitable support members include, but are not limited to, plastic, polyethylene, polypropylene, filter paper, glass fiber paper, quartz fiber paper, mineral paper, fiberglass, fabric, cellulose filter paper, and the like. The support member may fix the poly(acid) matrix in place by any convenient method. For example, the support member may affix the poly(acid) matrix in place by friction forces or by tension forces. Such support members and methods of using such support members include but are not limited to, those described in German Patent Publication No. DE4321904 B4, the discloser of which is herein incorporated, in its entirety, by reference.

The elongated structure may have a cap or other sealing element positioned at the first and/or second end. The cap may be configured as a snap cap, screw cap, or any other convenient configuration. Examples of elongated structures having such caps and sealing elements include, but are not limited to, those provided in the descriptions of the configurations and dimensions of the elongated structure.

In some instances, the elongated structure, e.g., a spin column, is present in a collection container, e.g., in a nesting relationship. The collection container may be a distinct structure, e.g., a collection tube, or a well or analogous structure of a multi-well plate. Examples of collection tubes configured to receive the elongated structure include, but are not limited to, those provided in the descriptions of the configurations and dimensions of the elongated structure.

Figure 2A:
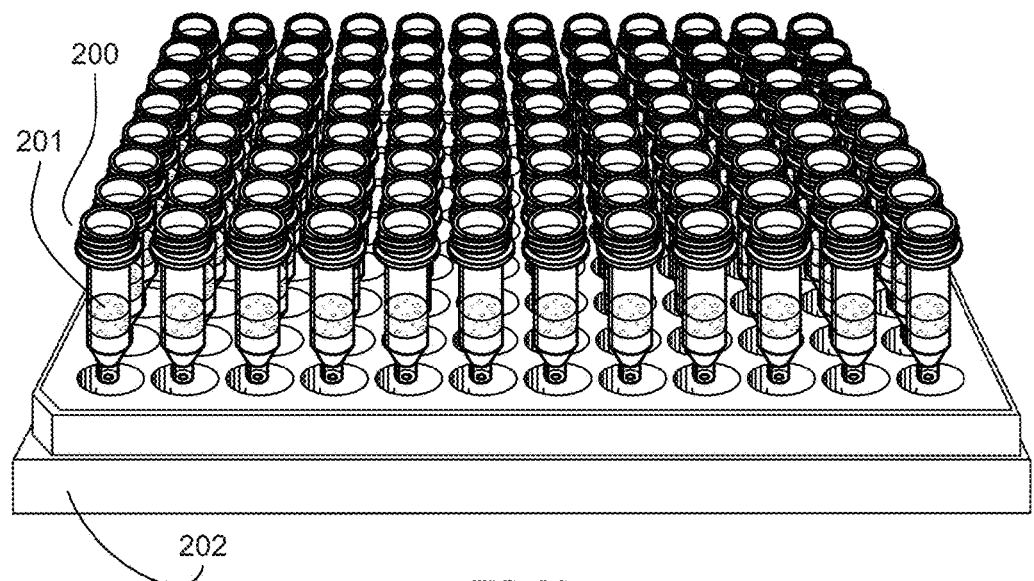
FIG. 2A-B provide views of spin columns arrayed in 96-unit format compatible with multi-well plates and capped and un-capped individual spin columns thereof.
Figure 2B:
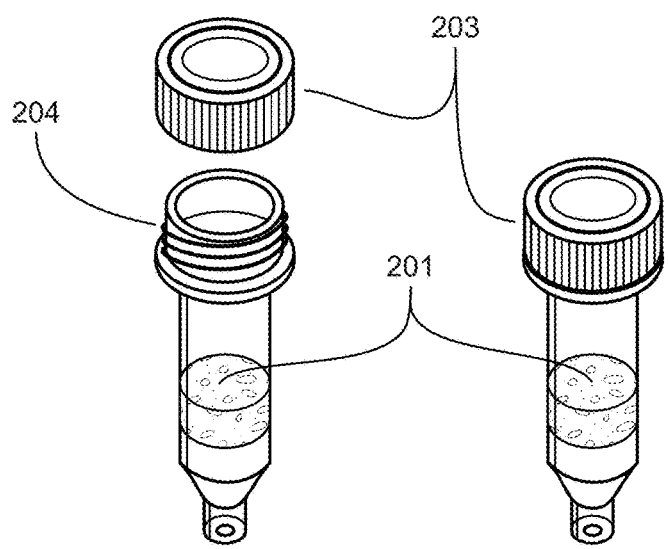

FIGS. 1 and 2 provide views of various spin column configurations, with collection tubes and multi-well plates. FIG. 1 provides images of exemplary spin column configurations of different sizes pictured side-by-side for comparison. The spin columns of FIG. 1 are pictured with corresponding collection tubes ranging from 2 mL to 50 mL volume and in both snap cap and screw top configurations. Also pictured with the snap cap spin columns of FIG. 1 are examples of support members configured as frits. FIG. 2A provides a view of exemplary spin columns (200) containing poly(acid) membranes (201) arrayed in a multiplexed configuration, e.g., to be compatible with a multi-well plate (202). FIG. 2B depicts views of both uncapped (left) and capped (right) individual spin columns containing poly (acid) membranes (201). Spin columns, e.g., as depicted in FIG. 2B, may be configured with threads (204) in order to be compatible with screw caps (203).

METHODS OF USING

Aspects of the invention further include methods of processing a liquid sample using spin columns of the invention, e.g., as described herein. Aspects of the methods include introducing the sample into a spin column having a poly(acid) matrix, e.g., as described above, through the sample inlet of the column; and moving the sample through the poly(acid) membrane to process the sample. The sample may be introduced into the column using any convenient protocol, e.g., by pipette. Sample movement through the column from the inlet to the outlet may be accomplished using any convenient protocol, e.g., by spinning the column, such as in a centrifuge, or by applying negative pressure to the sample outlet of the column, e.g., by applying a vacuum to the sample outlet, or by applying positive pressure to the sample inlet, e.g., by applying pressurized air, gas, or liquid to the sample inlet.

The method may be a method of separating one or more types of molecules, e.g., proteins, nucleic acids, etc., from a sample, or a method of separating one or more specific analytes from a sample. As such, in some instances the poly(acid) membrane is configured to bind to proteins in the sample and the method is a method of separating proteins from the sample. In some instances, the poly(acid) membrane is configured to bind to nucleic acids in the sample and the method is a method of separating nucleic acids from the sample. In some instances, the poly(acid) membrane is configured to specifically bind to an analyte of interest in the sample and the method is a method of separating the analyte from the sample. Analytes of interest may vary, e.g., proteins, a nucleic acid and small molecule, etc.

In certain instances, the method may further include charging or recharging the poly(acid) membrane before use. As described herein, charging of a poly(acid) membrane describes contacting the poly(acid) membrane with a metal ion that may complex with a chelating ligand to form a metal ion affinity complex. Any convenient medium containing the desired metal ion with which the poly(acid) membrane is to be charged may be utilized in charging or recharging the poly(acid) membrane. For example, in certain instances salts, e.g., salts of chlorides or sulfates, of a desired metal ion, e.g., $CuCl_2$, $NiCl_2$, $CuSO_4$, or $NiSO_4$, are dissolved in water or buffer to generate a suitable medium for charging the poly(acid) membrane. Methods of contacting of the poly(acid) membrane with the charging medium may vary and in some instances may include incubating the poly(acid) membrane with the charging medium and/or flowing the charging medium through the poly(acid) membrane, e.g., by gravity, by vacuum pressure, by positive pressure, or spinning the column, e.g., in a centrifuge. In certain instances, a poly(acid) membrane present in a spin column may have been previous charged with a particular metal ion, i.e., pre-charged, and subsequently stored before use in a ready-to-use format.

In some instances, the method may further include equilibrating the poly(acid) membrane prior to use. For example, a charged column may be contacted with one or more equilibration buffers. Equilibration buffers of the present disclosure may vary and are those buffers that prepare the poly(acid) membrane for the application of sample and optimal binding of the target to the affinity element. For example, in some instances, equilibration buffers of interest include but are not limited to solutions containing salts, e.g. sodium salts, e.g., sodium phosphate and/or sodium chloride, e.g., phosphate buffered saline (PBS). In some instances commonly used buffers may be employed, e.g., including but not limited to: Tris-HCl, Tris-acetate, HEPES, MOPS, sodium acetate, and the like. In some instances, chelating agents, e.g., ethylenediaminetetraacetic acid (EDTA), ethylene glycol tetraacetic acid (EGTA), citrate, etc., are excluded from, or if present are present in low amounts, equilibration buffers in order to increase binding of the target to the affinity element. In certain instances, an elution agent, e.g., imidazole, and/or a chelating agent is included in the equilibration buffer a low concentration, i.e., at a concentration lower than the concentration at which the agent is used for elution of the target, as a competitive binding agent in order to increase stringency of the poly (acid) membrane and decrease binding of undesired molecules, e.g., contaminates, to the affinity agent.

In certain instances, buffers of the present disclosure may include certain additional agents used for altering characteristics of a particular target or groups of targets in order to facilitate the purification of the target using the spin columns and methods described herein. Such additional agents may vary but will be those compatible with or present in amounts compatible with, i.e.

will not render the component unusable for its intended function at the amount at which the additional agent is present, the spin columns and the poly(acid) membranes as described herein. Such additional agents include but are not limited to reducing agents (e.g., dithiothreitol, dithioerythritol, β-mercaptoethanol, Tris[2-carboxyethyl] phosphine, glutathione, etc.), denaturing agents (e.g, urea, guanidine-HCl, etc.), detergents (e.g., Triton, Tween, NP-40, cholate, 3-[(3-Cholamidopropyl)dimethylammonio]-1-propanesulfonate, etc.), alcohols (e.g., ethanol, glycerol, etc.), and the like.

In some instances, the method may further include dissolving or diluting a sample in binding buffer prior to applying the sample to a spin column of the present disclosure. In some instances the binding buffer may have the same components as the equilibration buffer and may, in some instances, have the same composition as the equilibration buffer. In some instances the binding buffer may differ from the equilibration buffer by the presence or absence of one or more components. In some instances the binding buffer may differ from the equilibration buffer in the amount of one or more components. For example, in some instances the binding buffer may include more or less elution agent than the equilibration buffer in order to modulate binding stringency as desired. In some instances, the binding buffer may include more or less of a particular additional agent present in the elution buffer in order to increase or decrease a particular characteristic of the target in order to modulate binding stringency as desired.

In some instances the method may further include incubating the sample, either with or without binding buffer, in contact with the poly(acid) membrane in order to allow the target to bind the affinity agent. Such incubating may be performed after the sample is applied to the poly(acid) membrane by any convenient means, e.g., by pipetting the sample onto the poly(acid) membrane and allowing the sample to come into full contact with the poly(acid) membrane, e.g., through the action of gravity on the sample or by spinning the sample, e.g., in a centrifuge. Such incubations may be performed at an convenient temperature to increase binding of the target or to decrease non-specific binding, e.g. at room-temperature (RT), at 4° C., between 0 and 4° C., between 4° C. and 10° C., between 10° C. and RT, between RT and 37° C., between 37° C. and 55° C., between 55° C. and 95° C., or above 95° C.

In certain instances, the method may further include one or more washes with one or more suitable wash buffers. In some instances wash buffers may be the same as either the binding buffer and/or the equilibration buffer. In certain instances, a wash buffer will be different, either due to the presence or absence of a particular component or to the amount of a particular component, from the binding buffer or the equilibration buffer. In some instances the wash buffer may differ from the binding buffer or the equilibration buffer only in pH. In certain instances where multiple wash buffers are employed, the multiple wash buffers may differ in the presence or absence of one or more components, e.g., the presence or absence one or more additional agents described above, e.g., detergents, or the amounts of one or more components, e.g., wash buffers may contain differing amounts of an elution agent. In certain instances, multiple wash buffers may differ only in pH.

In some instances, the method further includes releasing bound molecules from the poly(acid) membrane, e.g., by elution, etc. Any convenient method may be utilized to release bound molecules from the poly(acid) membrane, e.g., through the use of an elution buffer containing an elution agent. Elution buffers of the present disclosure may vary and may, in some cases, may differ from the wash buffer, binding buffer, and/or equilibration buffer in the presence or absence or amount of only one component, e.g., the elution agent component. For example, in some instances, an elution buffer may be essentially the same as a previously described buffer but for having a higher concentration of an elution agent, e.g., from 1.5 to 100 times more elution agent, e.g., 1.5-2 times more, 2-5 times more, 2-10 times more, 5-10 times more, 10-20 times more, 20-50 times more, 50-100 times more. In other instances, the elution buffer may differ in more than one component from a previously described buffer and also include a higher concentration of an elution agent, e.g., from 1.5 to 100 times more elution agent, e.g., 1.5-2 times more, 2-5 times more, 2-10 times more, 5-10 times more, 10-20 times more, 20-50 times more, 50-100 times more. Elution agents of the present disclosure may vary but generally include any molecule capable of disrupting the binding between the target and the affinity element, including but not limited to molecules that competitively bind with the affinity element, i.e. competing agents (e.g., imidazole, imidazole derivatives, histidine, glycine, etc.), chelators (e.g., EDTA, EGTA, citrate, etc.), and the like. In some instances, an elution agent, e.g., a competing agent, may be present in an elution buffer at a concentration effective in releasing the bound molecules, e.g., proteins, from the poly(acid) membrane. Such effective concentrations vary and in some cases include concentrations ranging from 1 mM to 10 M, e.g., 1 mM to 10 mM, 1 mM to 100 mM, 10 mM to 100 mM, 10 mM to 0.5 M, 100 mM to 0.5 M, 200 mM to 0.5 M, 300 mM to 0.5 M, 400 mM to 0.5 M, 200 mM to 0.7 M, 0.5 M to 1 M, 1 M to 2 M, 2 M to 3 M, 1 M to 5 M, and 5 M to 10 M.

In some instances, releasing bound molecules may be achieved by disruption of the bond between the metal ion and the chelating ligand, i.e. metal ion stripping. Any convenient method of metal ion stripping may be used including, e.g., altering the pH of the solution surrounding the poly(acid) membrane. By lowering the pH is meant increasing the acidity of the solution surrounding the poly (acid) membrane which may be achieved by either flowing a new solution into the poly(acid) membrane, e.g., an elution solution with low pH, or by directly lowering the pH of the solution currently surrounding the poly(acid) membrane, e.g., by adding acid, e.g., concentrated acid. In some instances metal ion stripping is achieved by lowering the pH of the solution surrounding the poly(acid) membrane to within pH 2 to pH 8, including e.g., pH 2.5 to pH 7.5, pH 2 to pH 6, pH 3 to pH 8, pH 2 to pH 4, or pH 3 to pH 5. In some instances, following metal ion stripping, eluted molecules may be further purified, e.g., to remove the metal ions, by any convenient method, e.g., by desalting (e.g., by running through a desalting column), by buffer exchange, by precipitation, etc.

In some instances, the method further includes running the isolated molecule(s) through the same poly(acid) membrane in order to further purify the isolated molecules. For example, in certain instances, an isolated molecule, e.g., a protein, may be reapplied to the poly(acid) membrane and rebound to the membrane and re-eluted from the membrane. In certain instances, different buffers, e.g., higher stringency buffers, are used when an isolated molecule is re-run through a poly(acid) membrane. In certain instances one or more different columns, e.g., a new column, is used to further purify an isolated molecule where the different column may be the same type or different type of column used to initially purify the isolated molecule.

In certain instances, the method further includes analyzing the released molecule or analyte. Methods of analysis and/or detection useful in analyzing the released molecule may vary and include but are not limited to enzymatic assays (e.g., ELISA, anti-tag ELISA, anti-His ELISA, etc), gel assays (e.g., Western blot, dot blot assays, antibody (e.g., anti-His antibody) based assays, etc.), assays coupled with signal amplification, assays coupled with fluorescent detection and/or quantification, and the like. In certain instances, gel assays, e.g., SDS-PAGE gels, may be used to analyze the released molecule by staining the gel by any convenient method including but not limited to Coomassie staining, silver staining, deep purple staining, fluorescent staining, and the like. In some instances, analysis of the released molecule may be performed by functional assay, i.e., an assay that tests some functional property of the isolated molecule in order to detect its presence, measure its amount, or evaluate its purity. Functional assays useful in analyzing molecules, e.g., proteins, isolated according to the present disclosure may vary and include but are not limited to assays that assay the function of an isolated protein, e.g., enzymatic assays.

In some instances, the method further includes modifying a component of a sample, e.g., a protein or peptide, in a controlled manner by applying the protein or peptide to a poly(acid) matrix which contains a modifying agent, e.g., a protein or peptide modifying agent. Protein modifying agents include but are not limited to protein and peptide modifying enzymes and enzymes that act on protein and peptide modifications (glycosylations, acetylations, alkylations, methylations, biotinylations, glutamylations, glycylations, isoprenylations, lipoylations, phosphopantetheinylations, phosphorylations, sulfations, selenations, C-terminal amidations, etc.) and include but are not limited to: oxidoreductases, transferases, hydrolases, lyases, isomerases, ligases, polymerases, kinases, phosphatases, acetylases, deacetylases, methylases, demethylases, ubiquitinases, deubiquitinases, amylases, and proteases (e.g., serine proteases, threonine proteases, cysteine proteases, aspartate proteases, glutamic acid proteases, and metalloproteases, etc.) etc.

According to certain embodiments, modification agents of the present disclosure may be bound directly to the poly (acid) matrix or may be bound via an affinity element. In certain instances, controlled protein and peptide modification, e.g., controlled protein or peptide digestion, is achieved by controlling the rate or the amount of time a protein or peptide is exposed to a particular modifying agent thus controlling the rate and/or time of modification, e.g., protein or peptide digestion. In some instances, such control may be achieved by modulating the rate of exposure or the time of exposure of the protein or peptide to the protein modifying agent, e.g., protease, by controlling the flow of sample through the spin column. In some instances the spin column may restrict flow completely under ambient conditions such that the protein or peptide is exposed to protein modifying agent after the sample is applied to the matrix and until the sample is pulled from the membrane, e.g., by applying force, e.g., by spinning the column in a centrifuge. In some instances the spin column may restrict flow partially either under ambient condition or force-applied conditions such that the protein or peptide is exposed to protein modifying agent as the sample moves through the matrix, e.g., by force applied through gravity, positive pressure, vacuum pressure, or centrifugal force (e.g., applied through the use of a centrifuge) and the rate of exposure may be controlled by modulating the force that is applied to move the sample through the matrix. In some instances where a sample is moved through a matrix in order to control the rate of exposure to a modifying agent the sample may be completely removed from the matrix by applying an additional force or increasing an already applied force, e.g., through spinning the column in a centrifuge or increasing the speed of the centrifuge. In some instances, the protein to be modified may be bound to a poly(acid) membrane of a spin column as described elsewhere herein, and the modifying agent may be contacted with the poly(acid) membrane in a controlled manner, e.g., for a controlled amount of time or flowed through the membrane at a controlled rate. In some instances, the time or rate of exposure to the modifying agent may be controlled by modifying some component of the poly(acid) membrane, e.g., the thickness of the poly (acid) membrane, the porosity of the poly(acid) membrane, the polymer density of the poly(acid) membrane, etc. In some instances, modifying some physical property of the protein to be modified, e.g., modifying three dimensional structure of the protein, e.g., by subjecting the protein to denaturing conditions, may be used as an additional means of controlling the rate of protein modification. In some instances, a modified protein or peptide modified by controlled means, as described herein, may be further washed or eluted from the matrix according to the wash and elution methods described previously herein.

In some instances, the method further includes reusing and/or recharging the poly(acid) membrane. In other instances the membrane may be directly reused without stripping/recharging, e.g., when the same target or analyte is to be bound. In some instances the elongated structure may be reused and the poly(acid) membrane replaced. In some instances the collection tube, as described herein, may be reused with a new or regenerated spin column.

Utility

Spin columns and methods as described herein find use in a variety of different applications, including but not limited to, protein purification applications, antibody purification applications, analyte detection applications, selective analyte enrichment applications, controlled protein and peptide digestion applications, controlled protein or peptide modification applications, environmental purification applications, etc.

In certain instances, spin columns and methods of the present disclosure may be used in research settings for the purification of individual analytes for research purposes or for non-diagnostic analyte detection applications. Isolation of such research analytes may be performed from research samples, i.e., laboratory derived research samples or laboratory generated research samples, where such samples are generated in a research laboratory. Such research samples may be used as a source of desired non-diagnostic analytes, i.e., analytes that are not obtained from or derived from a living multi-cellular organism, e.g., mammal, in order to make a diagnosis. In other words, the sample has not been obtained to determine the presence of one or more disease analytes in order to diagnose a disease or condition. Non-diagnostic samples of interest include those obtained from in vitro sources, e.g., cell cultures, tissue cultures, non-diagnostic animal tissue samples or body fluids (i.e., such samples when not being used for diagnosis). In certain instances, the complexity of a particular non-diagnostic sample requires that a non-diagnostic analyte be isolated or purified from the sample in order to allow for the efficient detection of the analyte.

In certain instances, spin columns and methods of the present disclosure may be used in clinical settings for the isolation of disease analytes. Disease analytes may be isolated from diagnostic samples, i.e. samples derived from an organism, e.g., a plant, an animal, a mammal, etc., in order to diagnose the presence of a diagnostic analyte and subsequently allow for the diagnosis of a disease or condition. In certain instances, the complexity of a particular diagnostic sample requires that a diagnostic analyte be isolated or purified from the sample in order to allow for the efficient detection of the analyte. Diagnostic samples, from which a diagnostic analyte may be isolated, include but are not limited to: tissues samples, blood, urine, semen, feces, saliva, mucus, sputum, lacrimation, cerebral spinal fluid, lymph, bile, gastric acid, and the like. In certain instances, a diagnostic sample must be first processed, e.g., homogenized, ground, lysed, diluted, or concentrated, prior to being applied to a spin column of the present disclosure. In other instances, a diagnostic sample may be applied directly to a spin column without pre-processing.

In certain embodiments, following binding of a diagnostic analyte to the spin column, the diagnostic analyte is not eluted from the poly(acid) membrane and detection of the analyte is performed directly on the poly(acid) membrane. Detection of a diagnostic analyte on the poly(acid) membrane may be performed by any convenient means and may, e.g., consist of contacting the membrane with a detection agent, e.g., with a member of a second member of binding pair, e.g., an antibody, an antigen, a ligand, a receptor, etc., or with a second member of a reaction pair, e.g., a substrate, an enzyme, etc., that generates or makes possible the generation of a detectable signal when a threshold quantity of diagnostic analyte is bound to the poly(acid) membrane. Such detection of a diagnostic analyte concentrated on a poly(acid) membrane of a spin column of the present disclosure allows for the detection of analytes not normally present at sufficiently high concentration to be detected in diagnostic samples by conventional means without either analyte amplification or detection signal amplification.

In certain instances, spin columns and methods of the present disclosure may be used in the application that require selective enrichment of certain target analytes. For example, certain target analytes, e.g., non-diagnostic analytes, diagnostic analytes, or environmental analytes, may be enriched using spin columns or methods as described herein based on some general characteristic, e.g., physical characteristic or chemical characteristic (e.g., $pK_a$, $pK_b$, hydrophobicity, size, electrical charge, phosphorylation status, ubiquitination status, etc.), shared by a number of different target analytes in a sample such that the product of enrichment may be utilized in downstream applications, e.g., further analysis or further enrichment or purification. In some instances such further downstream applications are not efficient or non-function, e.g., individual analytes or individual aspects of individual analytes may not be detected, without prior selective enrichment. For example, in some instances spin columns and methods of the present disclosure find use in selective enrichment of certain target analytes prior to downstream applications including but not limited to: proteomic applications, peptide sequencing applications, mass spectrometry applications, electron transfer dissociation applications, tandem mass spectrometry applications, high-performance liquid chromatography applications, matrix-assisted laser desorption/ionization applications, and the like.

In certain instances, spin columns and methods of the present disclosure may be used in the isolation of analytes from environmental samples, i.e., samples derived from the environment. As used herein, environmental samples specifically exclude research samples or other samples derived in a laboratory setting for research purposes. Environmental samples from which an environmental analyte may be isolated using the spin columns and methods described herein include but are not limited to air samples, particulate samples, water samples (i.e., rain water samples, freshwater samples, seawater samples), and soil samples. In certain instances, an environmental sample may be applied directly to a spin column for the isolation of an environmental analyte as described herein without pre-processing of the sample. In some instances, and environmental sample is first processes, e.g., ground, diluted, concentrated, dissolved, adsorbed, etc., prior to being applied to a spin column.

In certain embodiments, following binding of an environmental analyte to the spin column, the environmental analyte is not eluted from the poly(acid) membrane and detection of the analyte is performed directly on the poly(acid) membrane. Detection of an environmental analyte on the poly(acid) membrane may be performed by any convenient means and may, e.g., consist of contacting the membrane with a detection agent or with a second member of a reaction pair that generates or makes possible the generation of a detectable signal when a threshold quantity of environmental analyte is bound to the poly(acid) membrane. Such detection of an environmental analyte concentrated on a poly(acid) membrane of a spin column of the present disclosure allows for the detection of analytes not normally present at sufficiently high concentration to be detected in environmental samples by conventional means without either analyte amplification or detection signal amplification.

In certain instances, spin columns and methods of the present disclosure may be used in environmental purification applications. For example, spin columns capable of binding one or more environmental analytes, such as those discussed above, may be used for the purification of the environmental sample where removal of a particular environmental analyte or analytes is desired. Such particular environmental analytes that may be removed from environmental samples are those environmental analytes for which specific or non-specific affinity elements are known that bind the analytes and include but are not limited to: environmental toxins, pollutants (e.g., heavy metals, persistent organic pollutants, environmental persistent pharmaceutical pollutants, polycyclic aromatic hydrocarbons, chlorinated hydrocarbons, volatile organic compounds, environmental xenobiotics, fertilizers, pesticides, herbicides, sewage, dirt, etc.), and organisms (e.g., invasive organisms, disease causing organisms, etc.). In certain embodiments, spin columns and methods of the present disclosure may be utilized by flowing one or more environmental samples, e.g., water, through such spin columns for the purpose of generating a purified, i.e. analyte-free or essentially analyte free, environmental sample.

In certain instances, spin columns and methods of the present disclosure may be used in protein purification applications, e.g., isolation of recombinant proteins or isolation of natural proteins. Recombinant proteins that may be isolated using spin columns and methods of the present disclosure vary widely and include those recombinant proteins produced or grown in the laboratory. In some instances, recombinant protein samples from which recombinant proteins are isolated may be samples obtained from laboratory organisms, e.g., plants or animals, or cultures of laboratory organisms, e.g., bacterial cultures, yeast cultures, cell cultures, algae cultures, marine organism cultures, etc., that are the result of bioengineering, i.e. express recombinant or mutant proteins not normally found in the wild-type organism, i.e. not found in the host organism in nature.

Spin columns and methods of the present disclosure find use in the rapid isolation of proteins for screening applications, e.g., for high-throughput screening applications. According to certain embodiments, a plurality of proteins of interest, e.g., a library of mutant or recombinant proteins, may be isolated in a multiplexed configuration to allow for the high-throughput screening of the plurality of proteins for particular protein functions or characteristics, e.g., binding to a particular substrate, fluorescence, enzymatic activity, processivity, etc. Multiplexed configurations of interest include but are not limited to spin columns in arrays of 96 units, 384 units, or 1536 units. Pluralities of proteins of interest may vary and may be generated according to any convenient method including but not limited to random or directed mutagenesis of an organism or a genome of an organism or a gene of an organism or an artificial gene. In certain instances, a plurality of proteins isolated using spin columns and methods of the present disclosure may be used directly in proteomic applications.

Spin columns and methods of the present disclosure find use in the rapid isolation of molecules, e.g., proteins, produced in industrial settings. For example, spin columns and methods of the present disclosure may be used to isolate molecules generated, e.g., grown, in large amounts, including, e.g., batch scale amounts, pilot scale amounts, or process scale amounts. Molecules produced in industrial settings may be synthetic molecules, engineered molecules (e.g., recombinant proteins), or naturally occurring molecules. For example, in certain instances, synthetic proteins or synthetic peptides produced by peptide synthesis methods, e.g., liquid-phase peptide synthesis or solid-phase synthesis, may be purified using the spin columns and methods described herein in order to remove impurities or remove incorrect synthesis products, e.g., truncated peptides, deletion peptides, undesired isomers, undesired side products, and the like.

In some instances, recombinant proteins or peptides, e.g., as described herein as generated in research laboratories, may be generated in industrial settings in large amounts, e.g., in batch scale amounts, pilot scale amounts, or process scale amounts. Any convenient method of cellular or cell-free protein or peptide synthesis may find use in generating proteins which can be isolated using columns and methods described herein including but not limed to proteins generated by: in vitro synthesis, e.g., cell-free in vitro protein synthesis; vivo synthesis, e.g., through protein biosynthesis; or growth in a bioreactor. In other instances, natural molecules, e.g., naturally occurring proteins or peptides, may be isolated in industrial settings using spin columns and methods described herein. For example, natural proteins or peptides that may be isolated include but are not limited to proteins grown in naturally occurring organisms, e.g., bacteria, archaea, or eukaryotes (e.g., animals, molds, fungi, plants, or protozoa). In some instances, proteins of interest that may be isolated include but are not limited to enzymes (e.g., oxidoreductases, transferases, hydrolases, lyases, isomerases, ligases, endonucleases, nucleases, polymerases, DNA modifying enzymes, light emitting enzymes, kinases, phosphatases, acetylases, deacetylases, methylases, demethylases, ubiquitinases, deubiquitinases, amylases, proteases, cellulases, etc.) fluorescent proteins, pigment proteins, cell signaling proteins, signal transduction proteins, ligand binding proteins, protein hormones, antibodies, protein and peptide antigens, structural proteins, and the like. Industries where proteins isolated using spin columns and methods of the present disclosure find use include but are not limited to the biotechnology industry, the pharmaceutical industry, the chemical industry, the food production and food processing industry (e.g., fermentation related food processing (e.g., baking, brewing, cheese making, yogurt making, etc.) and food extract and juice production), the vitamin and nutraceuticals industry, the biofuels industry, the paper industry, the agricultural industry, and the like.

Spin columns and methods of the present disclosure find use in controlled protein and peptide processing applications, including e.g., controlled protein and peptide digestions, controlled protein and peptide modification, and the like. For example, spin columns and methods of the present disclosure may be utilized to control the exposure of a particular sample containing proteins, particular proteins, or a particular protein to a protein modifying agent described herein. In certain instances, spin columns and method of the present disclosure applied to controlled protein and peptide modification applications may find use in modifying or digesting proteins or peptide for further analysis or processing in applications including but not limited to: proteomic applications, peptide sequencing applications, mass spectrometry applications, electron transfer dissociation applications, tandem mass spectrometry applications, high-performance liquid chromatography applications, matrix-assisted laser desorption/ionization applications, and the like.

Kits

Aspects of the invention also include kits for use in practicing the subject methods. The kits at least include a spin column, e.g., as described above. The kits and systems may also include a number of optional components that find use in the subject methods. Optional components of interest include buffers, including extraction/loading/washing buffer or buffers (e.g., as described above), containers, e.g., collection tubes and/or multi-well plates, and the like. Furthermore, the kits and systems may include reagents for producing affinity peptide tagged polypeptides, e.g., vectors encoding metal ion affinity peptides, such as those disclosed in U.S. Pat. No. 7,176,298; the disclosure of which vectors are herein incorporated by reference. In the subject kits, the one or more components are present in the same or different containers, as may be convenient or desirable.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The following examples are offered by way of illustration and not by way of limitation.

EXPERIMENTAL

Materials:
Membranes Evaluated

Several 25 mm diameter membranes were evaluated. Hydrophilic, highly hydroxilated nylon membranes (LoProdyne® LP (nylon 6,6 membrane, Pall Corporation, Port Washington, N.Y.), 1.2 μm pore size, 110 μm thick). Membrane pores were modified with 3 different chemistries. Type 1 membranes were modified in a layer-by-layer (LBL) configuration with poly(acrylic acid)/polyethyleneimine/poly(acrylic acid) (PAA/PEI/PAA) polymers and functionalized with nickel-nitrilotriacetic acid (Ni-NTA) for quick purification of his-tagged proteins at very high binding capacities. Type 2 membranes were modified in a membrane bushes configuration with poly(2-methacryloyl succinate) polymers and functionalized with Ni-NTA for quick purification of his-tagged proteins at very high binding capacities. Type 3 membranes were functionalized with Trypsin for controlled protein digestion.

Spin Column Manufacturing

Membranes were cut to ~7 mm diameter discs and assembled into spin columns in different variations: single layer, double layer, triple layer, top side up, top side down, etc. After spin column assembly the effective filtration/binding area was ~5 mm in diameter.

Protein Samples

Various starting materials were used in the evaluation of the manufactured spin columns. Protein sample starting materials were either previously purified protein samples or whole cell lysates of cells expressing recombinant proteins. Previously purified protein samples used included *Aequorea coerulescens* GFP (AcGFP) protein expressed without an affinity tag (old GFP w/out tag), freshly purified 6× histidine-asparagine tagged AcGFP (6HN-AcGFP), and purified histidine tagged ubiquitin (His-Tagged Ubiqutin (HisU)) (Sigma-Aldrich, St. Louis, Mo.). Whole cell lysate protein samples used included cell lysate expressing 6HN-AcGFP and 6His-GFPuv.

Experiments/Results

Protein Purification from Whole Cell Lysates

Cells expressing 6HN-AcGFP were grown and pelleted by centrifugation. 0.25 g cell pellets were lysed in 4 mL xTractor Buffer (cell lysis buffer, Clontech Laboratories, Mountain View, Calif.). All centrifugation steps were carried out at 9000×g for 4 min. Type 2 (brush) single layer (top-side up) membrane spin columns were equilibrated using 3 washes with 500 μL of phosphate buffered saline (PBS). 600 μL and 900 μL of cell lysate were loaded into the separate equilibrated columns. Columns were subsequently washed twice with 300 μL of wash buffer II (20 mM $NaPO_4$, 0.15 M NaCl, pH 7.6). Following washing, protein was eluted from the columns with 2 applications of 300 μL of elution buffer (20 mM $NaPO_4$, 0.5 M imidazole, 0.5 M NaCl, pH 7.6). Sequential elutions were kept separate for individual analysis. Following elution, protein yield was determined to be 142 μg and 231 μg for the 600 μL and 900 μL lysate samples, respectively.

Figure 3:
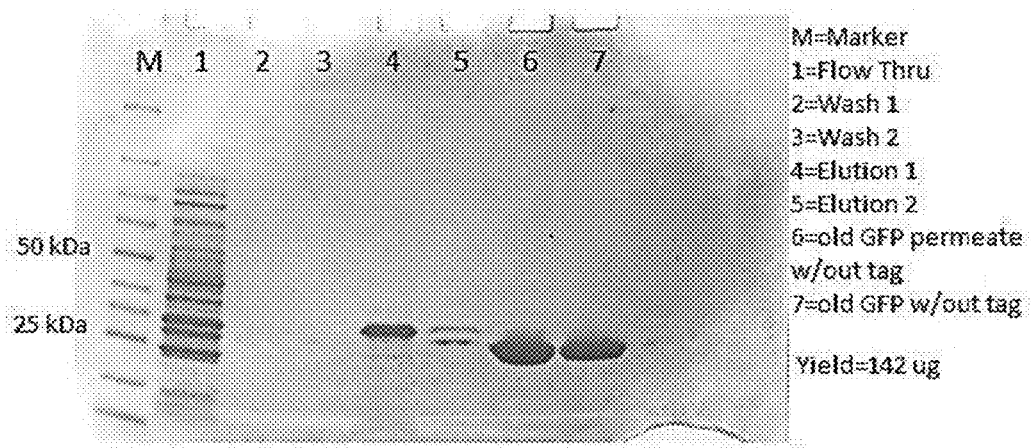
FIG. 3 depicts *Aequorea coerulescens* GFP (AcGFP) purified from 600 µL of cell lysate with Type 2 (Brush) membrane spin column in accordance with an embodiment of the invention.
Figure 4:
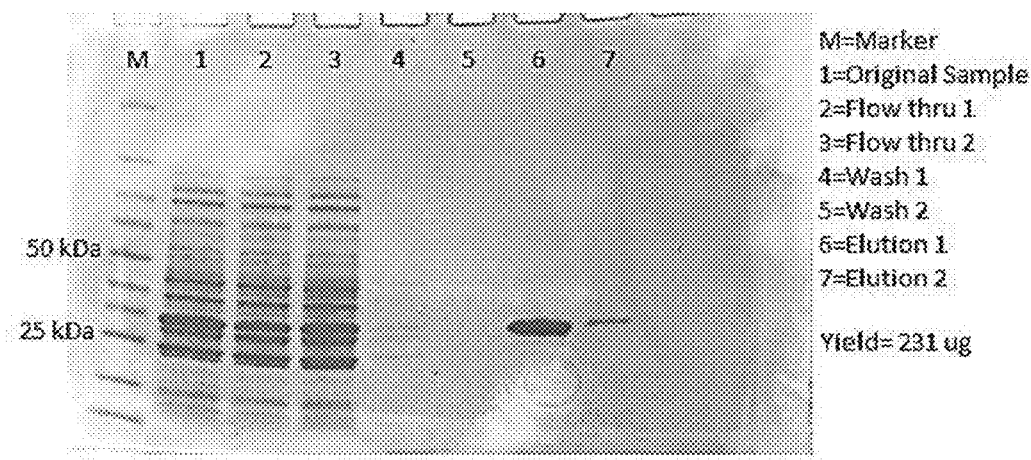
FIG. 4 depicts AcGFP purified from 900 µL of cell lysate with Type 2 (Brush) membrane spin column in accordance with an embodiment of the invention.

Protein gels were run to evaluate yield and purity for both the 600 μL (FIG. 3) and 900 μL (FIG. 4) cell lysate samples. Spin column performance was further evaluated by running both column flow through (Flow Thru) and column wash (Wash) on the gels. Previously purified untagged AcGFP (old GFP w/out tag) was run as a control.

Comparison of Various Spin Column Configurations and Target Proteins

Spin column performance was evaluated for spin columns manufactured with membranes in various orientations.

Protein purification characteristics of Type 1 (LBL) membrane spin columns with top-side up (up) and top-side down (down) membrane orientations were evaluated head-to-head and Type 2 (Brushes) membrane spin columns with top-side up (Top up) and top-side down (Top-down) membrane orientations were evaluated head-to-head. All centrifugation steps were performed at 11,000×g for 1 min. Each column was equilibrated with 2 washes of 400 μL PBS. Columns were loaded with 200 μL of cell lysate previously prepared for the above experiment. Spin columns were washed once with 300 μL of wash buffer I (20 mM $NaPO_4$, 0.1% Tween, pH 7.6) and once with 300 μL of wash buffer II (20 mM $NaPO_4$, 0.15 M NaCl, pH 7.6). Each spin column was eluted once with 300 μL of elution buffer (20 mM $NaPO_4$, 0.5 M imidazole, 0.5 M NaCl, pH 7.6). Following elution, protein yields were determined to be 34 μg, 47 μg, 115 μg, and 84 μg for Type 1 (LBL) membrane spin columns with top-side up and top-side down orientations and Type 2 (Brushes) membrane spin columns with top-side up and top-side down orientations, respectively.

Figure 5:
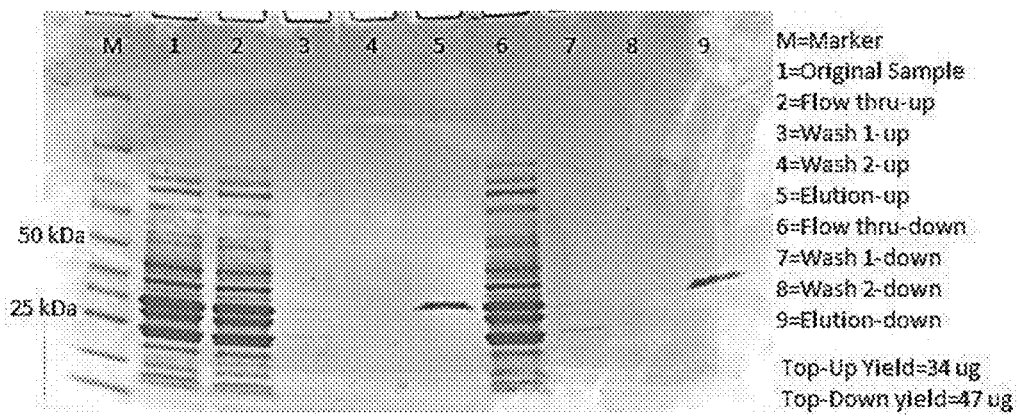
FIG. 5 depicts AcGFP purified from 200 µL of cell lysate with Type 1 (layer-by-layer (LBL)) membrane spin column with membrane in either a top-side up (up) or top-side down (down) configuration in accordance with embodiments of the invention.
Figure 6:
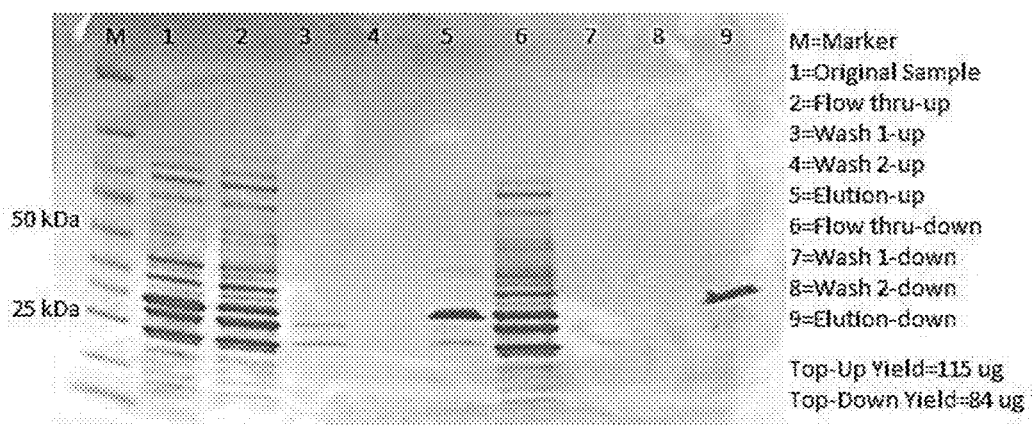
FIG. 6 depicts AcGFP purified from 200 µL of cell lysate with Type 2 (Brush) membrane spin column with membrane in either a top-side up (up) or top-side down (down) configuration in accordance with embodiments of the invention.

Protein gels were run to evaluate yield and purity for protein eluates of both the Type 1 (LBL) (FIG. 5) and Type 2 (Brushes) (FIG. 6) membrane spin columns. Top-side up and top-side down orientations were run head-to-head to evaluate relative protein purification characteristics of different membrane orientations. Spin column performance was further evaluated by running both column flow through (Flow Thru) and column washes (Wash) on the gels. The original samples were run as controls.

Spin column performance was evaluated for spin columns used to purify different target proteins.

Type 1 (LBL) membrane spin column protein purification characteristics were evaluated for the binding and elution of pre-purified of His-tagged ubiquitin. All centrifugation steps were performed at 11,000×g for 1 min. Each spin columns were equilibrated with 2 washes in 400 µL of protein dissolving buffer (PDB) (20 mM $NaPO_4$, pH 7.6). Each spin column was loaded with twice with 500 µL of 0.3 mg/mL of HisU in PDB. The permeate of each loading was reloaded three times. Spin columns were washed twice with 300 µL of wash buffer B (20 mM $NaPO_4$, 0.1% Tween, 0.15 M NaCl, pH 7.6). Protein was eluted twice with 300 µL of elution buffer.

Figure 7:
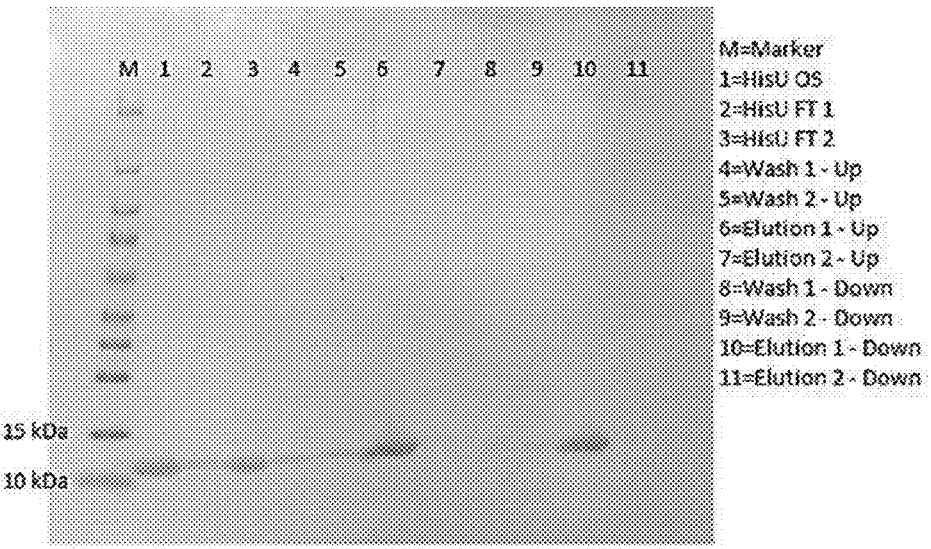
FIG. 7 depicts polyhistidine-tagged ubiquitin (HisU) purified with Type 1 (LBL) membrane spin columns with membrane in either a top-side up (up) or top-side down (down) configuration in accordance with embodiments of the invention.

A protein gel was run to evaluate yield and purity for protein eluates of both Top-side up (Up) and top-side down (Down) oriented membrane spin columns (FIG. 7). Spin column performance was further evaluated by running both column flow through (FT) and column washes (Wash) on the gel. The original sample (OS) was run as a control.

Head-to-head comparison of LBL and Brush type spin column performance was evaluated for binding and elution of pre-purified His-tagged ubiquitin.

LBL and Brush type spin columns were equilibrated and loaded with 400 µL of 1 mg/mL pre-purified His-tagged ubiquitin in buffer (20 mM phosphate, pH 7.4). Columns were washed twice with 400 µL of phosphate buffer. No protein was observed in the second wash. Proteins were eluted from the columns with 400 µL of 0.1 M EDTA.

Figure 8:
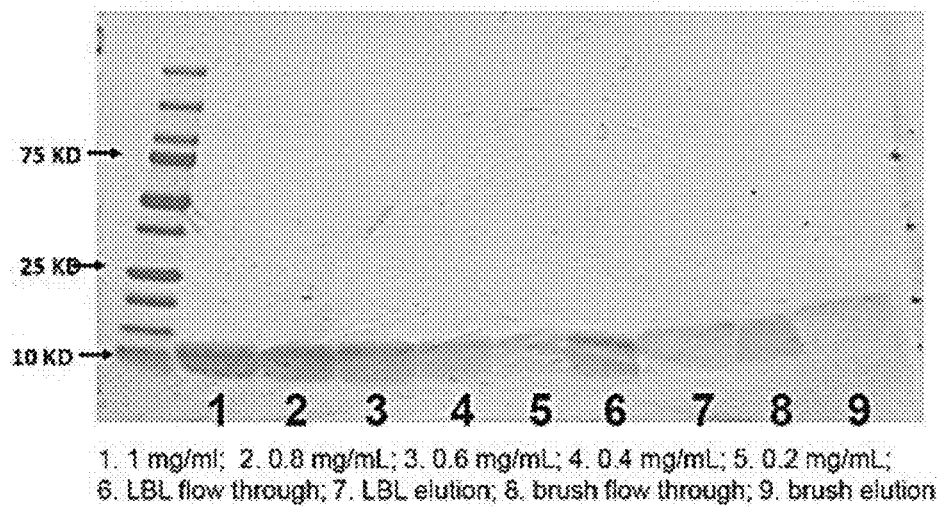
FIG. 8 depicts HisU purified with either LBL or brush membrane spin columns in accordance with embodiments of the invention.

A protein gel was run to evaluate yield and purity for protein eluates of both the LBL and Brush type spin columns (FIG. 8). Known concentrations of protein were run (FIG. 8, lanes 1-5) to allow for calibration and estimation of protein concentration in eluents. Spin column performance was further evaluated by running column flow through on the gel.

Evaluation of Spin Column Performance

Spin column performance was evaluated for spin columns with different membrane orientations.

Previously used Type 2 (Brushes) membrane spin columns with both top-side up and top-side down membrane orientations were stripped, regenerated and recharged. Columns were loaded with 900 µL of cell lysate and protein purification procedures were followed as previously described. Following elution, protein yield were determined to be 188 µg and 196 µg for top-side up and top-side down orientations, respectively. Yields for re-used membrane spin columns were thus similar to those seen on previously unused membrane spin columns.

Figure 9:
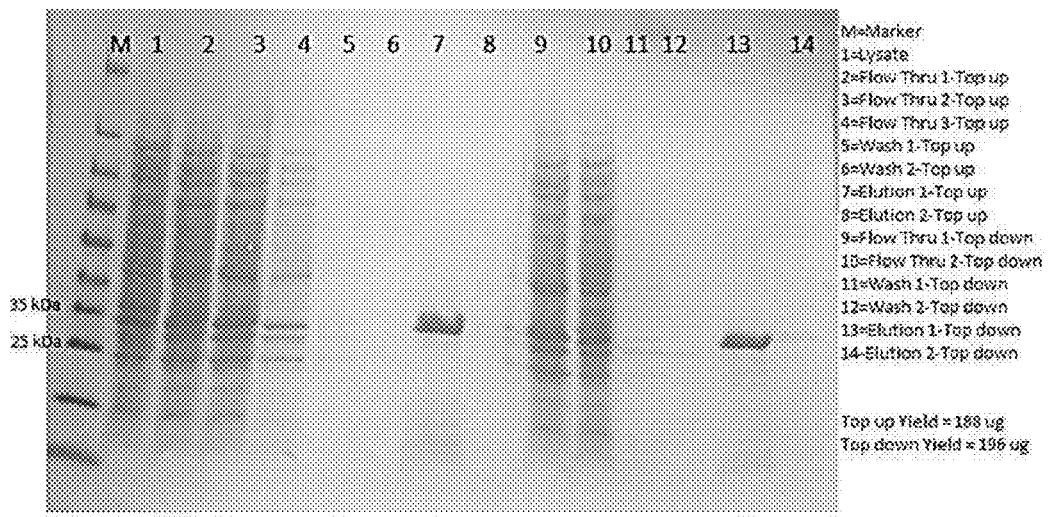
FIG. 9 depicts AcGFP purified from 900 µL of cell lysate with Type 2 (Brushes) membrane spin columns with membrane in either a top-side up (up) or top-side down (down) configuration in accordance with embodiments of the invention.

A protein gel was run to evaluate yield and purity for protein eluates of the spin columns (FIG. 9). Spin column performance was further evaluated by running column flow through and washes on the gel. The starting cell lysate was run on the gel as a control.

Spin column performance was evaluated spin columns with membranes with different numbers of layers and with the addition of 10 mM imidazole in the cell lysis buffer.

Type 1 columns with single layer membranes oriented top-side down (Sample 1-d) and Type 2 columns with double layer membranes oriented top-side up (Sample 2-2) were stripped, regenerated and recharged. Type 1 and Type 2 columns were loaded with 3.6 mL and 4.2 mL of cell lysate, respectively, along with 10 mM imidazole in the lysis buffer. Additional steps, e.g., washes and elutions, were performed as previous described. Following elution, protein yield were determined to be 49 µg and 300 µg for Type 1 and Type 2 columns, respectively. 88 µg of protein was measured in the final was before protein elution of the Type 2 column.

Figure 10:
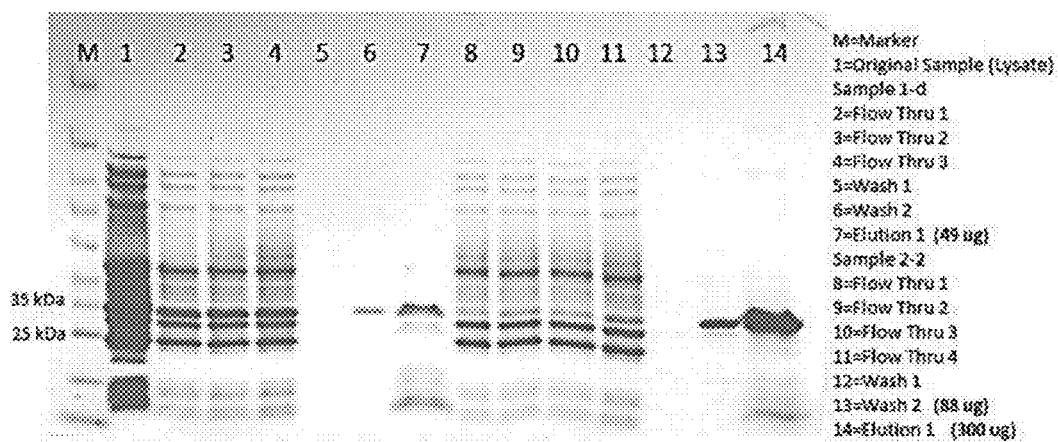
FIG. 10 depicts AcGFP purified from cell lysates using imidazole in cell lysis buffer using membrane spin columns with either a single layer top-side down (Sample 1-d) or double layer top-side up membrane configuration in accordance with embodiments of the invention.

A protein gel was run to evaluate yield and purity for protein eluates of the spin columns (FIG. 10). Spin column performance was further evaluated by running column flow through and washes on the gel. The original sample (Lysate) was run on the gel as a control.

Evaluation of Different Membranes

Spin column performance was evaluated for LBL membranes manufactured using 3-headed filtering device on manifold with peristaltic pump pulling reagents through. Small scale 47 mm LoProdyne® (nylon 6,6 membrane, Pall Corporation, Port Washington, N.Y.) membranes were prepared using Ni-NTA (NTA-lysine), nickel-iminodiacetic acid (Ni-IDA, no linker), and Ni-IDA-polyethylene glycol (PEG) (IDA with PEG linker). Spin columns were also prepared using 200 µL of TALON® (cobalt affinity resin, Clontech Laboratories, Mountain View, Calif.) resin. Membranes were cut using a standard hole punch with the membrane sandwiched between two pieces of paper. Membrane volume was 2.16 µL and TALON volume was 200 µL. Spin columns were assembled by hand, in-house.

Protein purification was performed as previously described from 500 µL of 6His-GFPuv expressing cell lysate. Protein yields were determined as indicated below in Table 1.

TABLE 1

| Spin Column | Wash (µg) | Elution Yield (µg) |
| --- | --- | --- |
| Ni-NTA | 13 | 84 |
| Ni-IDA | 42 | 32 |
| Ni-IDA-PEG | 27 | 27 |
| TALON | 60 | 189 |

Figure 11:
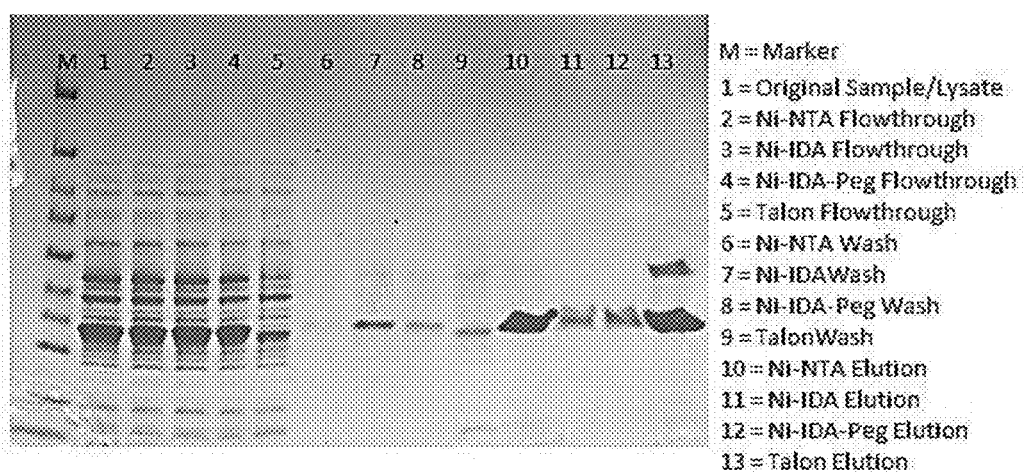
FIG. 11 depicts ultraviolet GFP (GFPuv) purified from 500 µL of cell lysate with various LBL membranes in accordance with embodiments of the invention.

A protein gel was run to evaluate yield and purity for protein eluates of the various spin columns (FIG. 11). Spin column performance was further evaluated by running column flow through and washes on the gel. The original sample lysate was run on the gel as a control.

Determination of Membrane Binding Capacity

Protein binding capacity was evaluated for LBL membranes manufactured using 3-headed filtering device on manifold with peristaltic pump pulling reagents through. Small scale 47 mm LoProdyne® (nylon 6,6 membrane, Pall Corporation, Port Washington, N.Y.) membranes were prepared.

Binding capacity assay was performed as follows. Purified 6His-GFPuv at 1.6 mg/mL in PBS buffer was exchanged into PDB and protein concentration was adjusted to 1 mg/mL with PDB. Membrane spin columns were loaded twice with 300 µL of protein. Centrifugation was performed at 4000×g for 1 min. Second flow through was reloaded onto membrane. Column was washed once with washing buffer I (20 mM phosphate buffer supplemented with 0.1% Tween-20) and once with buffer II (20 mM phosphate buffer supplemented with 0.15 M NaCl). Protein was eluted twice with 300 µL of elution buffer (20 mM phosphate buffer containing 0.5 M imidazole and 0.5 M NaCl). Protein yield was estimated by Bradford assay. Yield of purified 6His-GFPuv bound to the column was determined to be 79.3 µg and was eluted at 36.6 mg/mL. Protein amounts obtained from the 6His-GFPuv lysate elution and final wash were 84 µg and 13 µg, and the amounts obtained from the purified 6His-GFPuv elution and final wash were 79 µg and 15 µg, respectively.

Evaluation of Reproducibility of Membrane Performance

Spin column reproducibility was evaluated for LBL membranes manufactured using 3-headed filtering device on manifold with peristaltic pump pulling reagents through. Small scale 47 mm LoProdyne® (nylon 6,6 membrane, Pall Corporation, Port Washington, N.Y.) membranes were prepared unmodified and using the PAA/PEI/PAA polymer alone and with Ni-NTA or Ni-IDA. Three separate batches of Ni-NTA membranes were used. Two batches of Ni-NTA membranes were prepared on different days (Ni-NTA 1 and Ni-NTA 2) and two batches were prepared on the same day and stored at different conditions, standard conditions and −20 deg. C. (Ni-NTA 1 and Ni-NTA −20, respectively). Membranes and spin columns were prepared as previously described.

Protein purification was performed as previously described from 490 µL of 6His-GFPuv expressing cell lysate with the following minor variations: filtered water was used for all reactions and washes, membranes were dried in desiccator over calcium chloride overnight, and membranes were cut with a new hole punch. Protein yields were determined as indicated below in Table 2.

TABLE 2

| Sample | Wash (µg) | Elution (µg) | Elution from Previous Test (µg) |
| --- | --- | --- | --- |
| Unmodified | 44 | 0 | N/A |
| Polymer Only | 18 | 4 | N/A |
| Ni-NTA 2 | 14 | 97 | N/A |
| Ni-NTA 1 | 16 | 95 | 84 |
| Ni-NTA-20 | 16 | 95 | N/A |
| Ni-IDA | 18 | 13 | 32 |

Figure 12A:
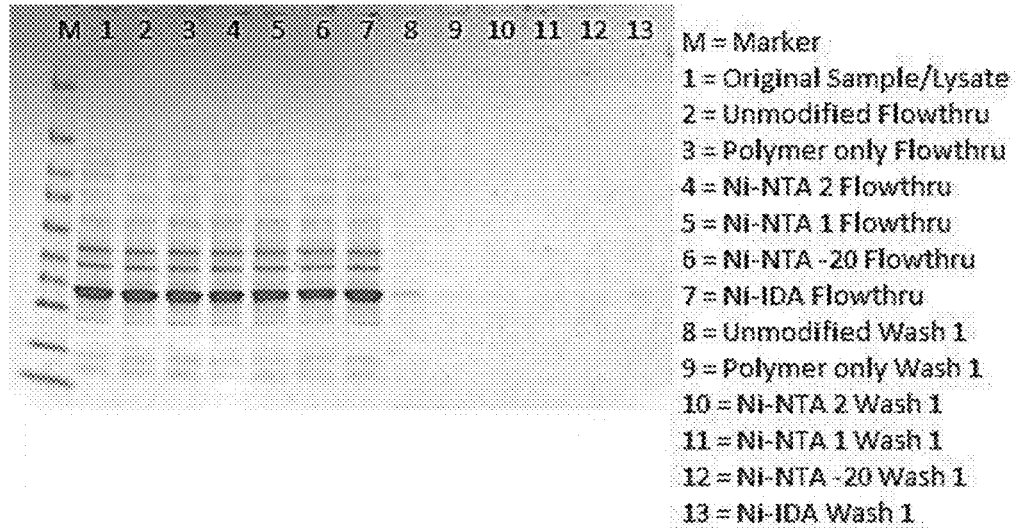
FIG. 12A-B depict GFPuv purified from 490 µL of cell lysate with various LBL membranes in accordance with embodiments of the invention.
Figure 12B:
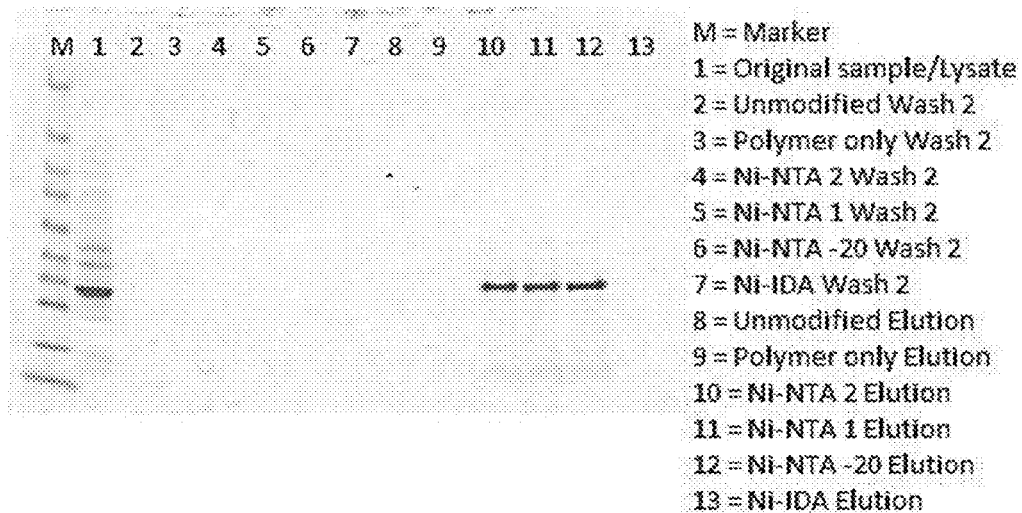

Protein gels were run to evaluate yield and purity for protein eluates of the various spin columns (FIG. 12A-B). Spin column performance was further evaluated by running column flow through and washes on the gels. The original sample lysate was run on the gels as a control.

Evaluation of Performance of Stacked Membranes

Spin column performance was evaluated for multi-layered LBL membranes manufactured using 3-headed filtering device on manifold with peristaltic pump pulling reagents through. Small scale 47 mm LoProdyne® (nylon 6,6 membrane, Pall Corporation, Port Washington, N.Y.) and SterliTech (Kent, Wash.) membranes were prepared as previously described and functionalized with Ni-NTA with slight modification. 1-Ethyl-3-[3-dimethylaminopropyl]carbodiimide hydrochloride (EDC) was added to N-hydroxysuccinimide (NHS) 4 minutes before use as compared to 8-10 minutes before use as in previous trials.

Spin columns containing three and five layers of stacked membranes were assembled by hand, in-house. Only a single layer of SterliTech membrane was used.

Protein purification was performed as previously described from 470 µL of 6His-GFPuv expressing cell lysate. Flow rates were reduced in multilayer membranes leading to increased contact times of 10%. Protein yields were determined as indicated below in Table 3.

TABLE 3

| Sample | Wash (µg) | Elution (µg) |
| --- | --- | --- |
| 1$^{st}$ layer of 5 layered LoProdyne membranes | 18 | 100 |
| 3$^{rd}$ layer of 5 layered LoProdyne membranes | 8 | 106 |
| 5$^{th}$ layer of 5 layered LoProdyne membranes | 17 | 91 |
| 1$^{st}$ layer of 3 layered LoProdyne membranes | 46 | 118 |
| 2$^{nd}$ layer of 3 layered LoProdyne membranes | 11 | 109 |
| Single layer of SteriTech membrane | 20 | 76 |

Figure 13A:
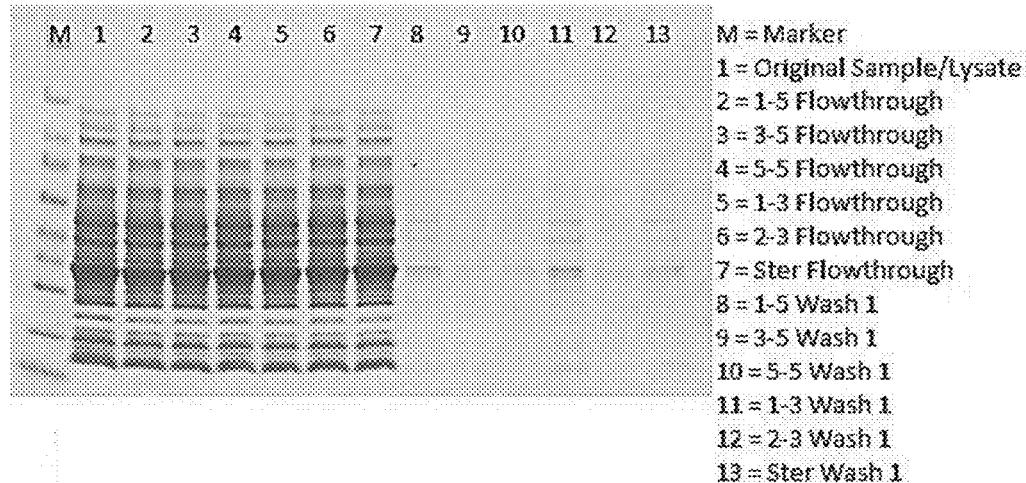
FIG. 13A-B depict GFPuv purified from 470 µL of cell lysate with various LBL membranes in accordance with embodiments of the invention.
Figure 13B:
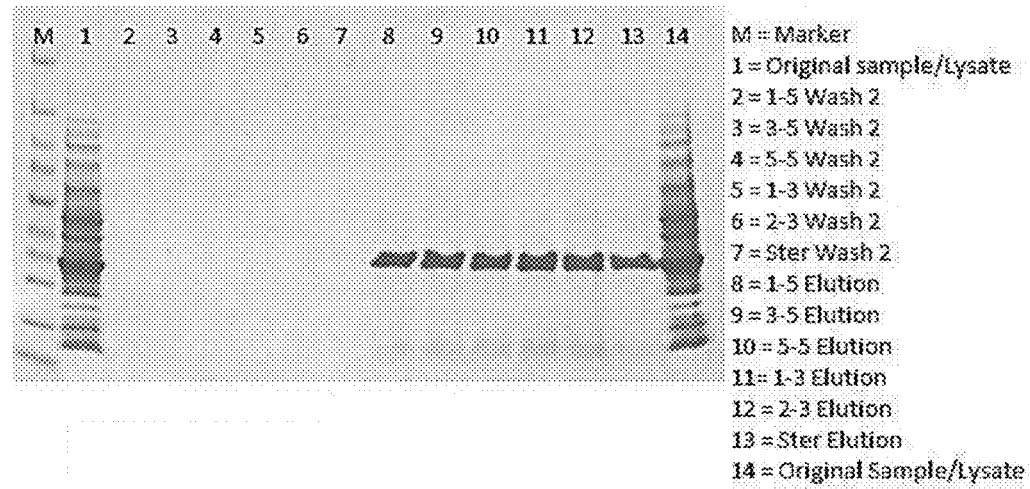

Protein gels were run to evaluate yield and purity for protein eluates of the various spin columns (FIG. 13A-B). As in Table 3 above, protein binding capacity of stacked membranes was evaluated individually. The individual membranes were labeled as follows: the first layer of the five layer membrane spin column (1-5), the third layer of the five layer membrane spin column (3-5), the fifth layer of the five layer membrane spin column (5-5), the first layer of the three layer membrane spin column (1-3), and the second layer of the three layer membrane spin column (2-3). Spin column performance was further evaluated by running column flow through and washes on the gels. The original sample lysate was run on the gels as a control.

CONCLUSIONS

Type 1 and 2 membranes both effectively separated target proteins from pre-purified and crude cell lysates. Type 2 membranes have higher capacity, reaching up to ~106 mg/cm$^3$ binding capacity for His-Tagged AcGFP in initial trials. Type 2 membranes have longer sample contact time and Type 1 membranes have more rapid sample flow through. Top-side up versus Top-side down configuration does not significantly affect performance as membranes were capable of effective and rapid protein purification in either orientation. Membranes performance is significantly retained upon reuse and following storage. Multilayer membranes maintain protein purification capabilities, showing little variation in protein binding capacity regardless of individual membrane position within the multilayer stack.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A spin column comprising:
an elongated hollow structure having a sample inlet at a first end and a sample outlet at a second end; and
a porous membrane support comprising a poly(acid) component comprising a polyelectrolyte adsorbed to a surface of the porous membrane support, wherein the poly(acid) component comprises a non-specific affinity element and the porous membrane support is positioned in the elongated hollow structure such that fluid must flow through the poly(acid) component to traverse the structure from the first end to the second end, wherein the non-specific affinity element comprises a tag-binding specific affinity element that binds to an epitope tag, wherein the tag-binding specific affinity element is selected from the group consisting of: an anti-FLAG antibody, anti-HA antibody, anti-Myc antibody, anti-GST antibody, anti-GFP antibody, and anti-V5 antibody, or any combination thereof.

2. The spin column according to claim 1, wherein the poly(acid) component comprises a poly(acid) film.

3. The spin column according to claim 1, wherein the poly(acid) component comprises poly(acid) brushes.

4. The spin column according to claim 1, wherein the elongated hollow structure is a tube.

5. The spin column according to claim 1, wherein the poly(acid) component is positioned proximal to the second end.

6. The spin column according to claim 1, wherein the column has a volume ranging from 1 µl to 1 liter.

7. The spin column according to claim 1, wherein the spin column comprises a frit in supporting relationship to the porous membrane support.

8. The spin column according to claim 7, wherein the frit is separable from the elongated structure.

9. The spin column according to claim 1, wherein the spin column is nested in a collection tube.

10. The spin column according to claim 9, wherein the collection tube comprises a cap.

11. The spin column according to claim 1, wherein the spin column comprises a cap at the first end.

12. A method of processing a liquid sample, the method comprising:
introducing the sample into a spin column according to claim 1 through the sample inlet; and
moving the sample through the poly(acid) membrane to process the sample.

13. The method according to claim 12, wherein moving the sample through the poly(acid) membrane is performed in 4 minutes or less.

14. The method according to claim 13, wherein moving the sample through the poly(acid) membrane is performed in 1 minute or less.

15. The method according to claim 12, wherein moving the sample through the poly(acid) membrane to process the sample comprises centrifugation.

16. The method according to claim 12, wherein moving the sample through the poly(acid) membrane to process the sample comprises applying a vacuum to the second end of the structure.

17. The method according to claim 12, further comprising:
introducing an elution buffer into the spin column through the sample inlet; and
moving the elution buffer through the poly(acid) membrane in 4 minutes or less.

18. The spin column according to claim 1, wherein the polyelectrolyte comprises an anionic polyelectrolyte.

19. The spin column according to claim 1, wherein the polyelectrolyte comprises a cationic polyelectrolyte.

20. A kit comprising:
a spin column according to claim 1; and
a collection tube configured to receive the spin column in a nesting relationship.

21. A spin column comprising:
an elongated hollow structure having a sample inlet at a first end and a sample outlet at a second end; and
a porous membrane support comprising a poly(acid) component comprising a polyelectrolyte adsorbed to a surface of the porous membrane support, wherein the poly(acid) component comprises a non-specific affinity element and the porous membrane support is positioned in the elongated hollow structure such that fluid must flow through the poly(acid) component to traverse the structure from the first end to the second end wherein the non-specific affinity element comprises a tag-binding specific affinity element that binds to avidin, streptavidin, biotin, horseradish peroxidase, digoxigenin, alkaline phosphatase, fluorescein, isothiocyanate, and tetramethylrhodamine, or any combination thereof.

* * * * *